(12) United States Patent
Gildersleeve et al.

(10) Patent No.: US 10,849,785 B2
(45) Date of Patent: Dec. 1, 2020

(54) SYSTEMS AND METHODS FOR PROVIDING TEMPERATURE-CONTROLLED THERAPY

(71) Applicant: DJO, LLC, Vista, CA (US)

(72) Inventors: Richard Gildersleeve, Carlsbad, CA (US); Thomas Jerome Bachinski, Lakevill, MN (US)

(73) Assignee: DJO, LLC, Vista, CA (US)

( * ) Notice: Subject to any disclaimer, the term of this patent is extended or adjusted under 35 U.S.C. 154(b) by 789 days.

(21) Appl. No.: 15/208,513

(22) Filed: Jul. 12, 2016

(65) Prior Publication Data

US 2016/0317347 A1 Nov. 3, 2016

Related U.S. Application Data

(63) Continuation of application No. 13/418,197, filed on Mar. 12, 2012, now abandoned.

(51) Int. Cl.
*A61F 7/00* (2006.01)
*A61F 7/02* (2006.01)
(Continued)

(52) U.S. Cl.
CPC ............ *A61F 7/0085* (2013.01); *A61F 7/007* (2013.01); *A61F 7/02* (2013.01); *A61N 1/0484* (2013.01); *A61N 1/0492* (2013.01); *A61N 1/36021* (2013.01); *A61F 2007/006* (2013.01); *A61F 2007/0042* (2013.01); *A61F 2007/0064* (2013.01); *A61F 2007/0069* (2013.01); *A61F 2007/0076* (2013.01);
(Continued)

(58) Field of Classification Search
CPC .. A61F 7/0085; A61F 2007/0054–0069; A61F 2007/0075; A61F 2007/0076; A61F 2007/0086; A61F 2007/0095; A61F 2007/0096
See application file for complete search history.

(56) References Cited

U.S. PATENT DOCUMENTS 3,316,732 A 5/1967 Burton
4,118,946 A 10/1978 Tubin
(Continued)

FOREIGN PATENT DOCUMENTS

WO 2007088547 A2 8/2007

OTHER PUBLICATIONS

International Search Report and Written Opinion dated Sep. 23, 2013 in International Application No. PCT/US2013/029347.
(Continued)

*Primary Examiner* — Eugene T Wu
(74) *Attorney, Agent, or Firm* — Veros Legal Solutions, LLP

(57) ABSTRACT

Systems and methods provide air or gas-based temperature-controlled medical devices. The systems and methods may be applied to provide therapy to a patient suffering orthopedic or other injuries. Air or other gas is temperature-controlled and adjusted to meet a patient's physical needs and delivered the patient therapy site through a temperature regulated system including a therapeutic orthopedic wrap. Feedback mechanisms allow the caregiver or the patient to adjust the temperature of the gas. Other fluids may also be used. The systems and methods permit use of electrotherapy for enhanced therapy and injury recovery.

9 Claims, 19 Drawing Sheets

(51) Int. Cl.
*A61N 1/04* (2006.01)
*A61N 1/36* (2006.01)
*A61L 2/10* (2006.01)

(52) U.S. Cl.
CPC ............... *A61F 2007/0086* (2013.01); *A61F 2007/0095* (2013.01); *A61F 2007/023* (2013.01); *A61F 2007/0236* (2013.01); *A61F 2007/0258* (2013.01); *A61F 2007/0273* (2013.01); *A61F 2007/0285* (2013.01); *A61F 2007/0292* (2013.01); *A61F 2007/0298* (2013.01); *A61L 2/10* (2013.01); *F04C 2270/0421* (2013.01)

(56) References Cited

U.S. PATENT DOCUMENTS

| | | | |
|---|---|---|---|
| 4,146,933 A | 4/1979 | Jenkins et al. | |
| 4,452,247 A | 6/1984 | Hebert | |
| 4,523,594 A | 6/1985 | Kuznetz | |
| 4,908,248 A | 3/1990 | Nakashima et al. | |
| 5,033,136 A | 6/1991 | Elkins | |
| 5,031,418 A | 7/1991 | Hirayama et al. | |
| 5,179,943 A | 1/1993 | Hama et al. | |
| 5,197,294 A | 3/1993 | Galvan et al. | |
| 5,397,338 A | 3/1995 | Grey et al. | |
| 5,456,701 A | 10/1995 | Stout | |
| 5,865,841 A | 2/1999 | Kolen et al. | |
| 5,980,561 A | 11/1999 | Kolen et al. | |
| 5,989,285 A | 11/1999 | Devilbiss et al. | |
| 6,245,096 B1 | 6/2001 | Tomic-Edgar et al. | |
| 6,465,708 B1 * | 10/2002 | Augustine | A61F 7/02 602/2 |
| 6,497,720 B1 | 12/2002 | Augustine et al. | |
| 6,510,696 B2 * | 1/2003 | Guttman | A41D 13/005 62/259.3 |
| 6,519,964 B2 | 2/2003 | Bieberich | |
| 6,551,347 B1 | 4/2003 | Elkins | |
| 6,581,400 B2 * | 6/2003 | Augustine | A47G 9/0215 607/107 |
| 6,596,019 B2 | 7/2003 | Turner et al. | |
| 6,702,840 B2 | 3/2004 | Keller et al. | |
| 7,721,349 B1 | 5/2010 | Strauss | |
| 7,771,461 B2 * | 8/2010 | Schock | A61F 7/0053 607/104 |
| 8,676,330 B2 | 3/2014 | Simon et al. | |
| 2002/0026226 A1 * | 2/2002 | Ein | A61F 7/007 607/108 |
| 2002/0056281 A1 | 5/2002 | Bieberich | |
| 2003/0045918 A1 | 3/2003 | Turner | |
| 2003/0216728 A1 | 3/2003 | Stern et al. | |
| 2003/0229385 A1 * | 12/2003 | Elkins | A61F 7/0085 607/104 |
| 2004/0064169 A1 | 4/2004 | Briscoe et al. | |
| 2005/0075592 A1 | 4/2005 | Garon | |
| 2005/0107855 A1 | 5/2005 | Lennox | |
| 2007/0299489 A1 | 12/2007 | Francis et al. | |
| 2008/0077209 A1 | 3/2008 | Vardanega | |
| 2008/0168595 A1 | 7/2008 | Almqvist | |
| 2008/0249524 A1 | 10/2008 | Dunning | |
| 2009/0264969 A1 * | 10/2009 | Gammons | A61F 7/02 607/104 |
| 2009/0312676 A1 | 12/2009 | Rousso et al. | |
| 2011/0092890 A1 | 4/2011 | Stryker et al. | |
| 2013/0023971 A1 | 1/2013 | Smiley | |

OTHER PUBLICATIONS

European Extended Search Report dated Jun. 13, 2017 for European Patent Application No. 16196256.8.

* cited by examiner

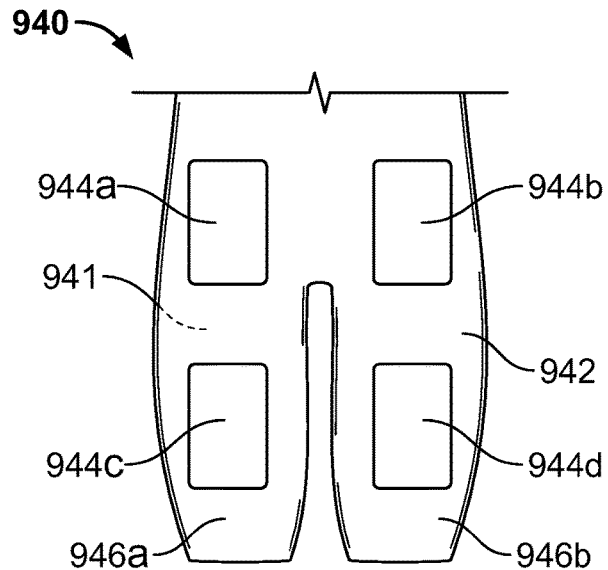
FIG. 15
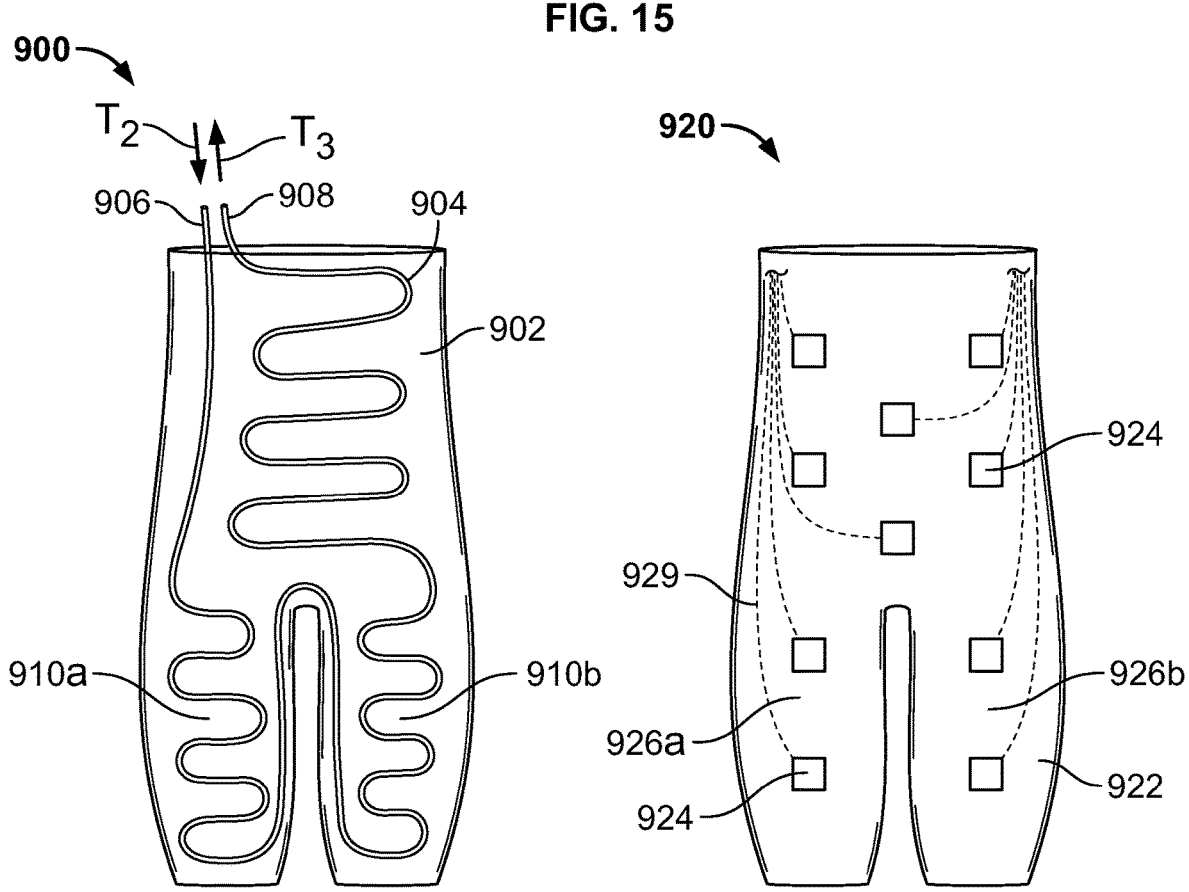
FIG. 16
FIG. 17

SYSTEMS AND METHODS FOR PROVIDING TEMPERATURE-CONTROLLED THERAPY

CROSS-REFERENCE TO RELATED APPLICATIONS

This application is a continuation of U.S. application Ser. No. 13/418,197, filed Mar. 12, 2012, which is incorporated by reference in its entirety.

BACKGROUND

Orthopedic injuries and extensive exercise are often accompanied by significant tissue swelling and muscle pain, which can lead to long-term and acute injuries. Various technologies have been employed to help provide therapy. For example, cold therapy products have long been used to provide therapy and rehabilitative care for orthopedic injuries. Cold therapy products include simple ice packs and more sophisticated fluid pumping machines that cool by circulating cold water through a therapeutic wrap. For example, the techniques described by Kolen, et al. (See U.S. Pat. No. 5,980,561) utilize ice water baths and pumping systems that pump fluid through orthopedic wraps along a patient's injury site to help manage tissue temperature in the site. Such techniques help address swelling, edema, and elevated temperatures at the injury site. Circulating cold water through the orthopedic wrap can help manage the swelling as the patient recovers. These techniques have been helpful, but they can be cumbersome for patients and physicians to use. For example, many techniques require use of a bucket of ice and cold water. The bucket can be awkward and heavy to transport, which can impair portability and mobility. Also, as the cold water circulates through the orthopedic wrap and along the patient's injury site, it warms and returns to the ice bath, where it melts the ice and ultimately raises the temperature of the bath. For long-term use, the ice must regularly be recharged and replaced in order to remain useful in managing swelling and temperature at the patient injury site. When the patient is under the supervision of a caretaker, such as a nurse, the caretaker must repeatedly add ice to maintain the proper cold therapy for patients. Additionally, the volume of water corresponding to melted ice must be removed. This regular maintenance adds physical strain to the patient or caregiver. It can also result in less effective therapy due to temperature variation or lapses in therapy until the ice is replaced.

Water-based systems have the tendency to leak, spill, or cause condensation at the therapy site. Water at the therapy site increases the likelihood of wound infection, and requires more frequent wound dressing changes. Leaks, spills, and condensation can also cause bedding or furniture damage, and in some cases, can damage the therapy system.

Moreover, while the temperature control can be effective in reducing swelling and pain, it does not necessarily address deeper-tissue pain. Deep tissue pain is traditionally treated with electrical stimulation using electrodes that deliver current to patient tissue. However, electro-stimulation systems are typically not configured for use with cold therapy. For example, water tends to condense around cold surfaces, and when used in conjunction with electrotherapy devices would cause corrosion and rusting around electrical components that would need to be used in electrical stimulation. Water at the electrical components could also cause undesirable electrical effects, including changes of electrical properties (such as impedance) and the formation of conductive shunt pathways (such as "short circuits") between components or to other parts of the body to render the stimulation ineffective, uncontrolled, or dangerous. Managing heavy ice buckets along with electro-stimulation controllers could also be cumbersome.

Improved techniques could be beneficial to the field, particularly as they provide for a longer, useful life of system components, provide a cooling or heating source and controller that are lighter weight, smaller size, and easier to manipulate, reduce or eliminate the risk of water at the therapy site, or provide a more compatible interface for cold (or heat) therapy and electrical stimulation systems.

SUMMARY

Systems and methods are disclosed herein that provide temperature-controlled medical devices that use air or other gas as a cooling or heating therapy fluid. The systems and methods provide therapy for a patient suffering orthopedic or other injuries. In general, the systems and methods provide a therapy fluid at a controlled temperature to meet a patient's physical needs. The fluid is delivered to the patient therapy site through a therapeutic orthopedic wrap. The systems and methods preferably include a temperature regulator and feedback mechanism to allow the caregiver or the patient to adjust the temperature of the fluid delivered to the therapy site. The systems and methods preferably use a gas-based fluid, such as air, that helps protect or reduce corrosion around the components of the system and the components of the therapy wrap to help them retain a longer useful life. In certain embodiments, an electrical stimulation module is applied to the patient injury site and used in combination with the temperature-controlled therapy to help to further enhance the options for pain management and injury recovery.

In general, a gas delivery system is disclosed for providing therapy to a patient. In certain implementations, the system includes a housing having a gas intake port, a means for adjusting and controlling temperature of the gas within the housing, and a means for delivering temperature-controlled gas to a therapy site. Certain implementations include a system for delivering a temperature-controlled gas to a therapy site using a gas temperature regulator, a gas intake port, and a coupling tube, having a first end configured to receive gas from the regulator and a second end configured to deliver gas to a therapy pad at a controlled temperature. The system is configured for use with a therapy pad, having a first surface that mates with the patient's therapy site and one or more straps or fasteners that connect the pad to the therapy site. The temperature regulator may be disposed within the therapy pad to provide an on-board pain management solution. The system may also include a tube disposed within the therapy pad and positioned in fluid communication between the temperature regulator and the intake port. In certain embodiments the intake port is a manifold in communication with ambient air, and ambient air is used as the fluid for fluid therapy.

In certain embodiments, the temperature regulator is a thermoelectric device, such as a Peltier device, and has a cooling component and optionally a heating component. The system, including the cooling and heating components, may be enclosed in a single housing. The single housing includes a first side and a second side disposed opposite the first side, the first side having an interface with a first flow tube and the second side having an interface with a second tube that can receive fluid from the regulator. The first tube is preferably connected to the first side to receive fluid from the cooling component, while the second tube receives fluid from the heating component. In certain embodiments, the first tube and second tube are joined at a valve and flow into the valve via a first portion of the coupling tube, and the valve has an output tube comprising a second portion of the coupling tube that connects to the therapy pad.

In certain embodiments the therapy pad has at least one aperture through which fluid is expelled from the pad. The at least one aperture may include a plurality of apertures, and those apertures may be disposed along a length and width of an inner surface of the pad. The plurality of apertures could also be disposed within respective ones of a plurality of indentations within the lower surface of the pad. For example, the pad surface could have a plurality of indentations in the form of an egg crate pattern with periodic undulations.

Other pad implementations are also contemplated. For example, the pad may be at least partially constructed of foam. It may also be enclosed within a frame having gas reliefs that allow gas to flow away from the therapy site. The pad could also have a diffusion plate disposed between the coupling tube and therapy pad, wherein the diffusion plate is structured to distribute the gas delivered to the therapy site.

The systems can also be configured for use with an electrode for providing electrical stimulation therapy. In certain embodiments, a system includes a connector structured to receive an electrode for delivering a current to the therapy site. In certain implementations, the connector is positioned on the inner surface of the therapy pad near or abutting the patient's tissue. The connector may be a female snap receptacle that receives an electrode having a male fitting for snapping to the receptacle. In certain implementations, the connector is mounted within a wall of the wrap. The first surface of the pad may also include at least one hole through which gas can flow from the temperature regulator, and the connector can be positioned adjacent the at least one hole so its mated electrode sits within the stream of therapy gas, which allows the system to provide fluid therapy and electrical stimulation to the same tissue site.

The systems can be configured with both fluid therapy and electrical stimulation components. In certain implementations, the fluid therapy and electrical stimulation components are configured within the therapy pad, providing a fully-integrated, on-board pain management system that provides both surface therapy (e.g., via temperature-controlled gas) and deep tissue therapy (e.g., via electrical stimulation). The on-board system includes a battery or other power source and tubing and electrical circuitry necessary to power the fluid temperature control, pump the fluid to the therapy site, and provide electrical stimulation to the therapy site.

Other components can also be included. For example, a blower may be provided to pump the gas to the therapy site. The blower is configured to deliver gas from the temperature regulator to the therapy site at any appropriate velocity. For example, the blower may be configured to deliver the gas at a velocity of at least 1 meter per second, between about 2 and about 5 meters per second, or between about 1 and about 10 meters per second. In alternative implementations, the blower can be configured to deliver the gas at velocities less than 1 meter per second or greater than 10 meters per second, as determined to be appropriate for effective temperature regulation of the therapy site.

The system can also be configured for more complex applications. For example, heating and cooling could be provided in combination. In those implementations, the coupling tube could include a first coupling tube section having a first end configured to receive a first gas from the temperature regulator and a second end configured to deliver the first gas to a first therapy pad component; and a second coupling tube section having a first end configured to receive a second gas from the temperature regulator and a second end configured to deliver the second gas to a second therapy pad component. The first gas is cooled by the regulator and the second gas is heated by the regulator. The gas could be distributed to a plurality of therapy pads. For example, it could be provided to a first pad configured to mate with a first therapy site; and a second pad configured to mate with a second therapy site on that patient (e.g., knee and torso). The pads could be provided to different patients, for example a cooling pad could be placed on one patient and a heating pad on another, with the fluid delivered to both being generated by the same regulator.

In certain embodiments, the temperature sensor monitors the temperature of the therapy site and delivers electrical signals to the regulator for adjusting the fluid temperature. The temperature regulator has a controller that receives information from the temperature sensor and triggers an alarm when a signal from the sensor indicates that the temperature at the therapy site has reached or exceeded a predetermined temperature. The temperature regulator is configured to trigger an automatic shutoff mechanism when the temperature at the therapy site reaches a predetermined temperature. In certain embodiments, the automatic shutoff mechanism is triggered when the therapy has been applied for a predetermined amount of time. In certain embodiments, the temperature sensor is attached to the therapy pad. The temperature sensor could be an infrared diode or other suitable product.

Improved flow tubing structures are also contemplated. In certain embodiments, a flow structure is configured for delivering a temperature-controlled gas to an orthopedic therapy pad and includes a flow tube with a foam inner surface defining an inner diameter, a foam outer surface defining an outer diameter, and an inner coil being coaxial with the tube, the coil having a self-expandable feature. The coil is disposed within a portion of at least one of the foam inner and foam outer surfaces. The structure of the walls reduces flow loss to provide sufficient air flow velocities. For example, the foam inner surface may be substantially smooth, which allows more efficient flow. The inner coil can be disposed between the foam inner and foam outer surfaces, or have at least a portion of the inner coil located along the foam outer surface, or at least a portion of the inner coil located along the foam inner surface. The flow tube inner diameter is preferably between about 0.25 and about 0.75 inches, or at least between about 0.1 and about 2 inches. When used in one or more systems disclosed herein, the tubing mates with a diffusion plate which distributes temperature-controlled gas to a therapy pad.

Other improved flow structures include tubing interconnects for an orthopedic gas delivery device. Example interconnects include a foam tube, having a first foam material and a first aperture, and a foam coupling having a second foam material and a first end that mates with the first aperture of the foam tube with an interference fit. The first aperture of the foam tube has an inner diameter, and the first end of the foam coupling has an outer diameter that mates with the inner diameter of the first aperture. The first aperture of the foam tube has an outer diameter, and the first end of the foam coupling has an inner diameter that mates with the outer diameter of the first aperture. The interconnects are thermal insulators that enhance thermal efficiencies of the flow circuit by reducing external heat transfer. The first and second foam materials could both be insulated foam, and could be substantially the same foam. For example, the thermal conductivity of the thermal insulation materials may be less than about 0.08 watts per meter-kelvin. These structures can also be used in the systems and methods described herein.

Methods of use and methods of operating a device are also contemplated. Certain methods provide temperature-controlled therapy to a body site by the steps of receiving gas into a housing, cooling a portion of the gas within the housing, and flowing the cooled gas from the housing through a first tube and into contact with a first body site. The methods may also include heating a portion of the gas within the housing and flowing the heated gas through a second tube and into contact with a second body site. The cooled gas and heated gas could be mixed in a valve, with the mixed gas delivered through a third tube to the body site. The methods also contemplate measuring a temperature of skin at a patient body site during therapy and sending a signal indicative of the measured temperature to a temperature regulator within the housing. Electrical current is then provided to the housing to adjust the temperature of the gas, based on the signal. The gas temperature is adjusted by changing a polarity of a component within the housing based on the temperature signal. A thermoelectric temperature control device, such as a Peltier device, could be used to heat and cool the gas.

The gas is delivered to the therapy site, preferably directly into contact with the site through a pad having at least one hole (and preferably a plurality of holes). The at least one hole is preferably aligned substantially over and in contact with the first body site so gas can flow to the first site through the one or more holes. An electrode can be positioned on the body site (or on multiple body sites), and the method can include sending electrical signals to the body site by the electrode while flowing cooled gas to that body site and the electrode. The same method steps can be performed using heated gas, including positioning an electrode on a second body site while flowing heated gas to the second body site. Certain implementations use ambient air as the therapy gas.

Methods of controlling the temperature of an orthopedic device are also contemplated, including receiving gas in a temperature regulator within the orthopedic device; providing an electrical current to the temperature regulator to adjust temperature of the receiving gas; and expelling the gas from the orthopedic device after adjusting the temperature of the gas. The method can include flowing the temperature-adjusted gas through a plurality of holes in the device, wherein the plurality of holes are exposed to the atmosphere. A portion of the gas may be cooled within the temperature regulator to a first temperature below ambient air temperature. A portion of the intake gas is heated within the temperature regulation to a second temperature that is higher than ambient air temperature. Temperature at a patient site is detected and a signal is sent to the temperature regulator and compared to a threshold that identifies a suitable temperature range for the expelled air.

The systems can be configured with a sterilization unit to provide sterilized gas. In certain implementations, the sterilization system includes a sterilization device such as an ultraviolet light source, a filter, or an ionization purifier. For example, the ultraviolet light source may be a germicidal bulb or an ultraviolet LED. The filter may be a high-efficiency particulate air (HEPA) filter, ultra low penetration air (ULPA) filter, or activated carbon filter. The sterilization unit may be coupled to the therapy pad. In certain implementations, the sterilization unit includes a combination of an ultraviolet light source, a filter, and an ionization purifier.

In certain implementations, the sterilization unit is coupled to the coupling tube. In certain implementations, the sterilization unit is coupled to the temperature regulator. The sterilization unit may also be coupled to the gas intake port. In certain implementations the sterilization unit is replaceable or removable from the system, for example, through a slot in a fluid tube.

The systems can be configured with one or more temperature maintenance packs. In certain implementations, the temperature maintenance packs are coupled to the therapy pad, for example, along the bottom surface of the pad. The temperature maintenance packs may be pliable to conform to a therapy site. For example, the temperature maintenance packs may comprise one of water, glycols, hydroxyethyl cellulose, and silica in a sealed, flexible enclosure. In certain implementations, the pad includes at least one aperture positioned above a temperature maintenance pack so that fluid flows onto the pack after flowing through the at least one aperture. Certain embodiments of the pad include a plurality of apertures. The plurality of apertures may be disposed along at least two sides of a temperature maintenance pack.

The systems can also be configured to provide closed-loop temperature-controlled therapy using fluids, such as water. In certain implementations, the system includes a temperature regulator, a therapy pad, having a surface configured to mate with the therapy site, and a coupling tube, having a first end configured to receive fluid from the regulator and a second end configured to deliver fluid to the therapy pad at a controlled temperature. In certain implementations, the temperature regulator is a thermoelectric device, such as a Peltier cooler.

Variations and modifications will occur to those of skill in the art after reviewing this disclosure, where disclosed features may be implemented in any combination and subcombinations (including multiple dependent combinations and subcombinations), with one or more other features described herein. The various features described or illustrated above, including any components thereof, may be combined or integrated in other systems, moreover, certain features may be omitted or not implemented.

BRIEF DESCRIPTION OF THE DRAWINGS

The foregoing and other objects and advantages will be more appreciated fully from the following further description thereof with reference to the accompanying drawings. These depicted embodiments are to be understood as illustrative, and not as limiting in any way:

FIG. 15 depicts a garment for regulating skin temperature.

FIG. 16 depicts a temperature regulation garment with an integrated flow channel.

FIG. 17 depicts an integrated temperature control system within a garment.

DETAILED DESCRIPTION

To provide an overall understanding of the systems, devices and methods described herein, certain illustrative embodiments will now be described. The systems and methods disclosed herein provide air or other gas-based temperature-controlled medical devices. The systems and methods may be applied to provide therapy for a patient suffering orthopedic or other injuries. For the purpose of clarity and illustration the systems, devices and methods are described with respect to orthopedic injuries or other pain augments. It will be understood by one of ordinary skill in the art that the systems, devices and methods disclosed herein may be adapted and modified as appropriate, and that the systems, devices and methods described herein may be employed in other suitable applications involving medical device therapy systems and methods, and that such other additions and modifications will not depart from the scope hereof.

In general, the systems and methods provide pain and injury management systems that use temperature-controlled fluid adjusted to meet a patient's physical needs, and deliver that fluid to a patient therapy site through a temperature regulated system and a therapeutic orthopedic wrap. The systems and methods also preferably include feedback mechanisms to allow the caregiver or the patient to adjust the temperature of the fluid delivered to the therapy site. The systems and methods preferably use a gas-based fluid, such as ambient air, that helps protect or reduce corrosion around the components of the system, including those around the therapy wrap, to help them retain a longer life span. In certain preferred embodiments, using air or other gas, rather than water or other heavy liquids, allows an electrical stimulation module to be applied to the patient injury site and used in combination with the temperature-controlled therapy, to help to further enhance the options for patient therapy and injury recovery. Controlling moisture when using electrical stimulation components is necessary for safe and efficacious therapy.

Figure 1:
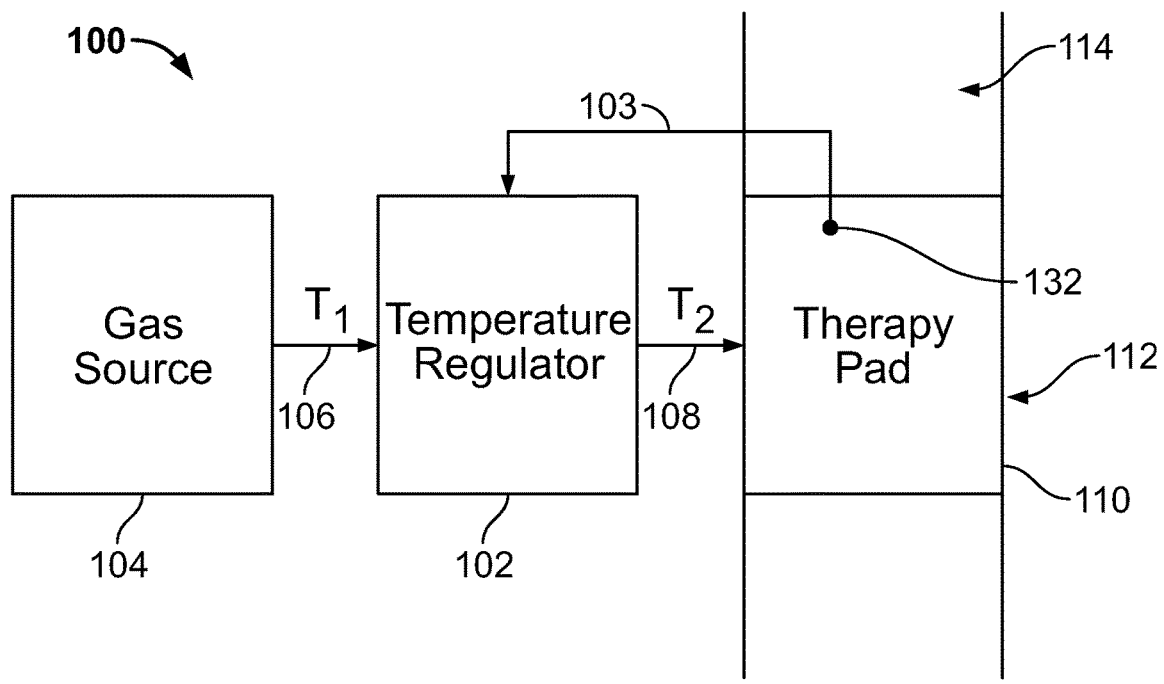
FIG. 1 depicts a control system for adjusting the temperature of a therapy gas in a therapy system for treating orthopedic injuries or other pain or trauma associated with exercise or other physical activity.

Certain implementations of the systems and methods are described in the figures below. These should be viewed as illustrative and not limiting. FIG. 1 illustrates a temperature control system used to control the temperature of a medical device or therapeutic fluid delivered by a medical device, such as a therapy pad for treating an orthopedic injury or other muscle, bone or ligament pain. The system 100 includes a temperature regulator unit 102 that receives gas or air from a gas source 104 and adjusts the gas or air temperature to a desired level for delivery to the patient. The gas source 104 may use, for example, compressed gas or ambient air. As shown, the temperature regulator 102 receives the gas through input line 106 at temperature ($T_1$) and delivers gas through an output line 108 at an output temperature ($T_2$). The system 100 also includes a temperature signal line 103 that is preferably an electrical line attached to a temperature sensor 132. In alternative embodiments, the system 100 provides temperature control for liquid fluids, such as water, in place of or in addition to gas temperature control. The liquid fluid may also be used to treat an injury site, as described herein.

The system 100 is configured to work with a therapy pad 110 for application on a patient 114 at an injury or therapy site 112. In use, the gas is input from the gas source 104 and its temperature is adjusted within the regulator 102 to output temperature $T_2$. The gas at temperature $T_2$ is then delivered to the pad 110 and the temperature of the patient's injury site 112 is detected by temperature sensor 132 located at or near the injury site 112. The temperature sensor 132 sends electrical signals by line 103 to temperature regulator 102, the signals being indicative of the temperature at the site 112. Those signals are used to adjust the fluid temperature inside the temperature regulator 102, and in turn, the temperature $T_2$ of gas delivered to the site 112. In preferred embodiments, the temperature $T_2$ of gas is adjustable, for example, within a range of 45-65° F.

In certain embodiments, the temperature regulator 102 acts independently of the temperature sensor 132. For example, the temperature sensor 132 may output the measured temperature to an LED display for the user (patient or caretaker) to see. Alternative embodiments do not include a temperature sensor. For example, the temperature regulator 132 may have operational ranges that may be selected by the user. Examples of selectable operational ranges may include settings for "Cold," "Warm," or "Hot" therapy. Alternatively, the temperature regulator may be controlled by a knob with a continuous selectable range from "Cold" to "Hot" therapy. The patient or user may provide feedback based on personal comfort levels and adjust the regulator 132 accordingly.

Figure 2:
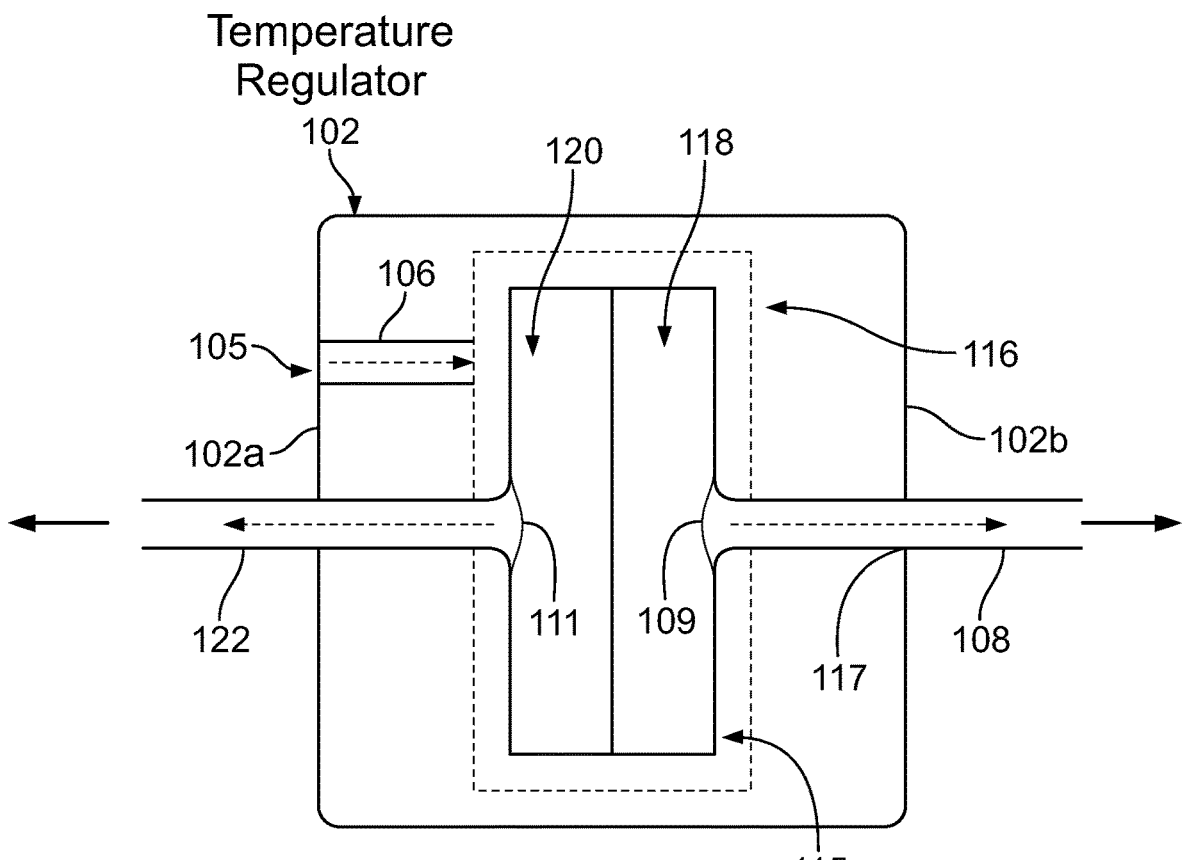
FIG. 2 depicts an example of a temperature regulator used in a system for controlling therapy gas temperature.

FIG. 2 depicts an example of a temperature regulator 102, which includes a temperature heating/cooling unit 115 having a cooling surface 118 and a heating surface 120 disposed and configured within a housing 116. In certain embodiments, the housing 116 is plastic. The temperature control unit 115 receives gas from the intake 105 through intake tubing 106 (for example, it could be ambient air or gas from an enclosed tank) and delivers the gas across one or both of the cooling surface 118 and heating surface 120. In the cooled air example, cooled air from the cooling surface 118 flows out of the control unit 115 and into the flow tube 108, for delivery to the pad. The temperature control unit 115 also includes a second output tube 122 that delivers heated air from the temperature control unit 115 to either vent in the atmosphere or flow back to the system for subsequent use at the patient site or otherwise with respect to the patient, as described more fully below. In certain embodiments, a liquid, such as water, flows through intake tubing 106, is heated or cooled at surfaces 118 or 120, and is delivered through tubes 108 or 122.

In certain implementations the temperature regulator 102 includes a plastic or polymer housing with inner walls, and the temperature control unit 115 is bolted or nailed or screwed or otherwise connected to these walls. The tubing 106, 108, and 122 are joined to the outer surface 102a and 102b of the temperature regulator 102 and to the walls of control unit 115 through interface orifices or ports that are disposed across those surfaces. For example, flow tube 108 fits through the wall of the temperature regulator 102b across the orifice 117. The tube 108 is also connected on its opposite end to the cooling surface 118 by the interface port 109. Similarly, the heating surface 120 has an interface port 111 (such as a funnel) through which warm fluid flows off the heating element and into the flow tube 122.

Figure 3A:
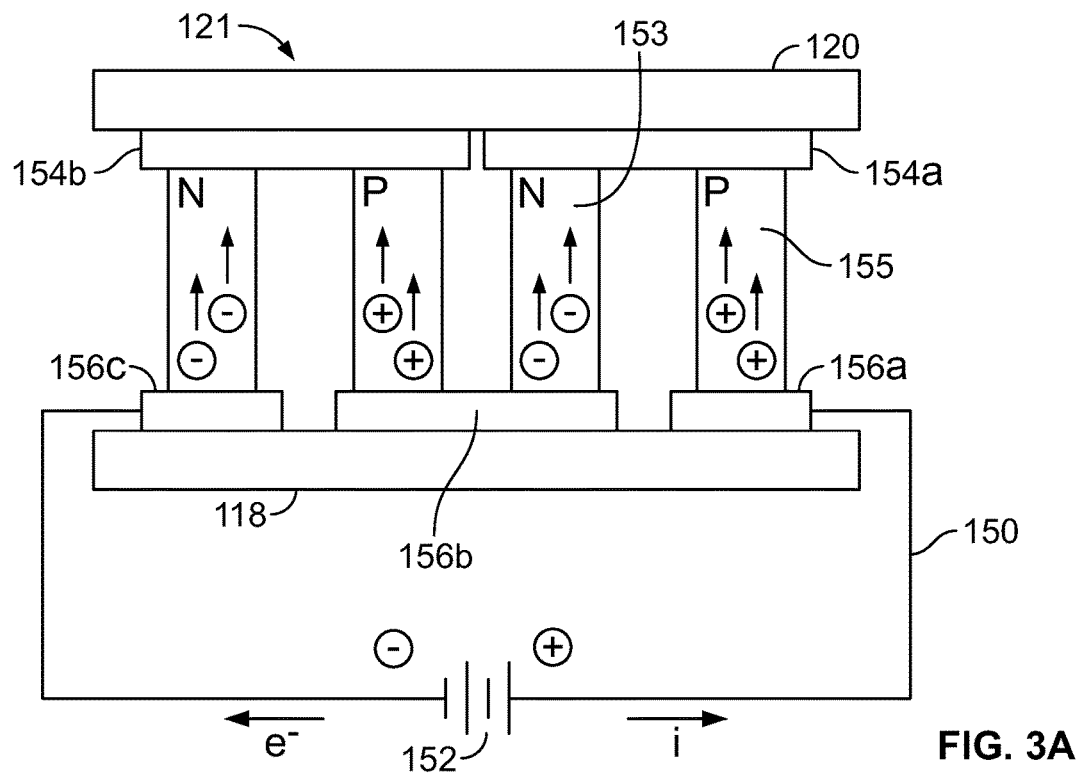
FIGS. 3A-3C depict examples of a thermoelectric temperature control system.

The temperature control unit 115 may be structured like a Peltier device, having a series of conductive and semiconductive plates through which direct current flows to adjust the temperature of a pair of outer surface plates. An example of a Peltier device 121 is shown in FIG. 3A. As shown, the device includes an N-type semiconductor plate 153 and P-type semiconductor plate 155. The N-type semiconductor plate, which serves as a carrier of "negative charge," has mobile electrons for carrying charge, and is preferably composed of a doped semiconductor material such as bismuth telluride or other suitable thermoelectric material. The P-type semiconductor plate, which serves as a carrier of "positive charge," has vacancies commonly referred to as "holes" for receiving electrons, and is preferably composed of an appropriately doped semiconductor material such as bismuth telluride or other suitable thermoelectric material. In an embodiment comprising a plurality of semiconductor plates 153 and 155, the plates are preferably placed in an alternating pattern as shown in FIG. 3A. As shown, the plates are preferably arranged in a parallel configuration relative to each other. The semiconductor plates 153, 155 are disposed between and electrically connected by metallic plates 154, 156 such that the current "i" (using conventional current notation, or "positive current" opposite the flow of electrons e⁻) flows through the lower metallic plate 156a, then through the P-type semiconductor plate 155, then through upper metallic plate 154a, then through the N-type semiconductor plate 153, then through the lower metallic plate 156b. As shown, this arrangement may repeat for any number of plates. The current may also be applied in the opposite direction.

The Peltier device 121 is electrically connected to a power source 152 within the circuit 150. In use, power source 152 delivers DC current "i" to plate 156a, which causes a net positive charge to flow via holes through the P-type semiconductor plate 155 to the metallic plate 154a and results in heat flow from metallic plate 156a to metallic plate 154a to raise the temperature of metallic plate 154a and lower the temperature of metallic plate 156a. Similarly, as the current "i" is delivered to N-type semiconductor plate 153, a net negative charge flows via electrons to the metallic plate 154a, which results in heat flow from metallic plate 156b to metallic plate 154a to raise the temperature of metallic plate 154a and lower the temperature of metallic plate 156a. In practice, the charge carriers (holes and electrons) flow in parallel directions and carry heat from one side of the device to the other. The device 121 includes heat transfer surfaces 118 and 120. As depicted, heat transfer surface 118 is a cooling surface composed of thermal material that abuts lower metallic plates 156a-156c, and heat transfer surface 120 is a heating surface composed of a thermal material that abuts upper metallic plates 154a-154b. As an example, surfaces 118 and 120 are composed of a ceramic material. In practice, the surfaces 118 and 120 provide heat storage and heat transfer from the metallic plates 154, 156 for adjusting the temperature of the delivered gas from temperature $T_1$ to temperature $T_2$. The surfaces 118 and 120 may also provide electrical insulation from the circuit. As depicted, surface 118 has a lower temperature than surface 120. However, either side may be used as a heating side or cooling side dependent on the direction of the current. Specifically, reversing the polarity of the current would result in surface 118 having a higher temperature than surface 120 because the charge carriers and, in turn, the heat, would flow in the opposite direction.

Figure 3B:
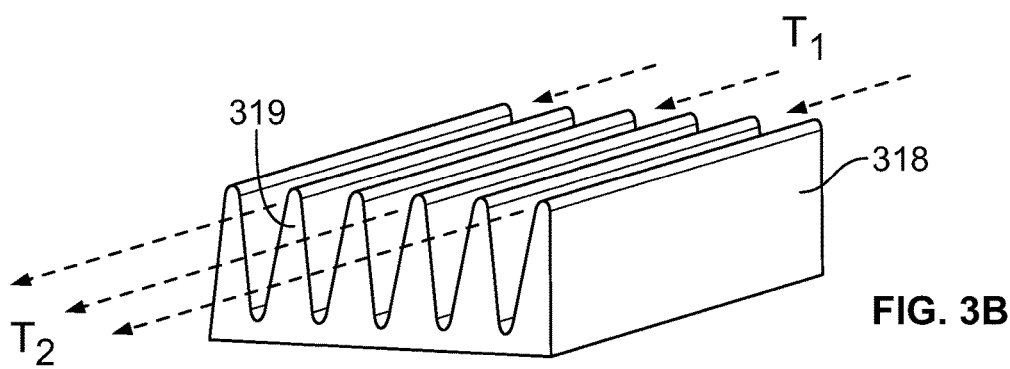

In practice, the temperature of the gas or other fluid is adjusted from temperature $T_1$ to temperature $T_2$ as it flows across heat transfer surfaces 118 and 120. In certain embodiments, as depicted in FIG. 3B, the heat transfer surfaces include structures to improve the efficiency of temperature regulation. For example, heat transfer surface 318, which is similar to surfaces 118 and 120 of FIG. 3A, may have ribs 319. The ribs 319 increase the surface area of surface 318, which provides increased contact for the gas to interface with the surface 318 to more rapidly and efficiently adjust the gas temperature. The ribs 319 of surface 318 may have other structures to improve heat transfer, including ridges, hatching, coils, teeth, and pores.

Figure 3C:
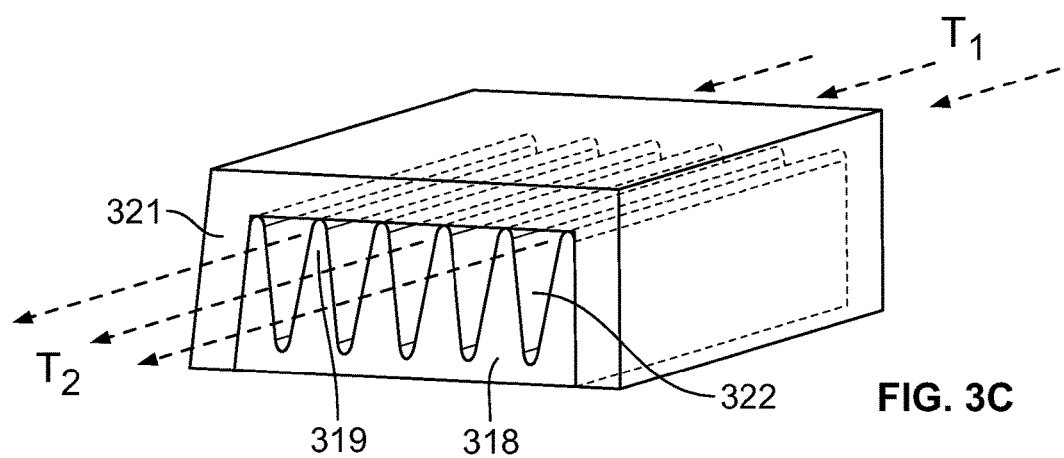

In the embodiment depicted in FIG. 3C, the heat transfer surface 318 includes an enclosure 321. When in place, the enclosure 321 forms closed channels 322 between the ribs 319 through which the gas or other fluid flows. Enclosure 321 may be formed of a thermally insulating material, such as Styrofoam, polyurethane foam, or other appropriate material to reduce heat exchange with the external environment. Minimizing external heat exchange improves efficiency, accuracy, and speed in regulating the temperature from $T_1$ to target temperature $T_2$ of the gas or other fluid. The enclosure 321 with channels 322 is particularly useful when heating or cooling a liquid, such as water to provide controlled flow.

Figure 4A:
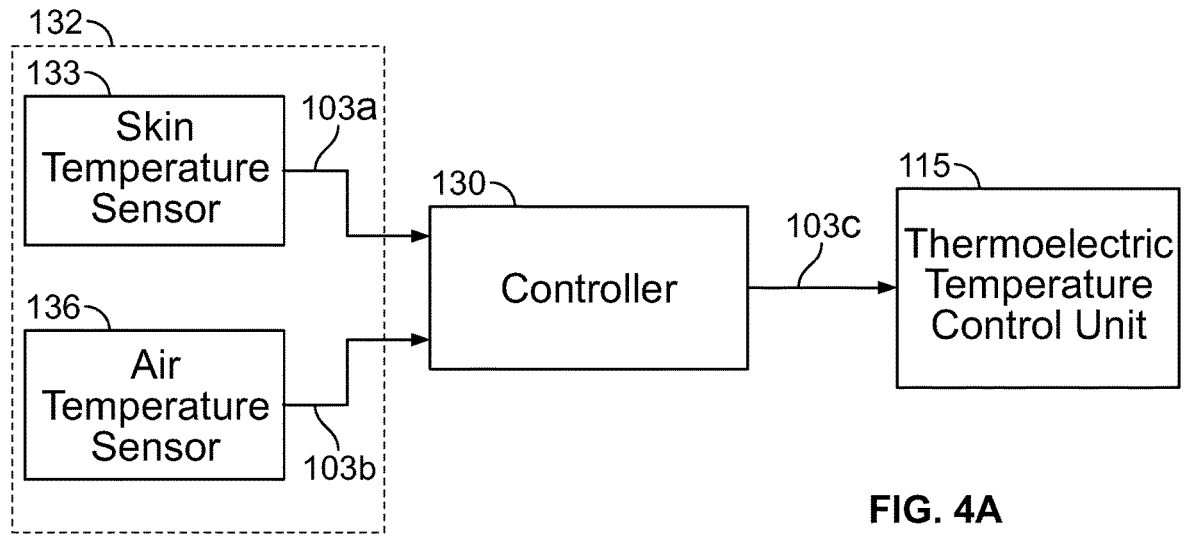
FIGS. 4A-4B depict an example of a thermoelectric temperature control unit and amplitude and frequency information for its application.

As indicated above, the temperature control unit 115 of temperature regulator 102 is preferably configured to be in electrical communication with the temperature sensor 132 through the electrical line 103. FIG. 4A depicts a schematic embodiment of a thermoelectric temperature control unit 115 in communication with the temperature sensor 132. The temperature sensor 132 includes at least one of a skin temperature sensor 133 and an air temperature sensor 136. In certain implementations, a sensor is provided having both a skin temperature sensor 133 and an air temperature sensor 136. In certain implementations, the skin temperature sensor 133 is an (IR) infrared diode. The IR diode provides the ability to measure skin temperature independent of the gas temperature. Additionally, the IR diode is able to measure skin temperature from thermal radiation without contacting the As shown in FIG. 4A, a controller 130, disposed within the electrical line 103, receives an input temperature sensor signal from the temperature sensor 132 along input electrical line 103, processes that signal, and converts it into a digital signal indicative of temperature at the therapy pad as detected by the sensor 132. For example, the controller 130 receives a temperature signal from skin temperature sensor 133 along line 103a. The controller may be a microcontroller, processor, or other computing device.

The controller 130 compares the digitized input signal to a threshold that may be programmed into the controller for establishing an appropriate and healthy range for the patient's skin temperature, and creates an output signal along line 103c that directs the thermoelectric temperature control unit 115 to increase or decrease the voltage across the voltage source 152, and thereby adjust the temperature of the gas being delivered from the temperature control unit 115. In certain embodiments the controller 130 stores the temperature measurements in storage media that is accessible during or after therapy. Storage media may include, but are not limited to, RAM, ROM, PROM (FPROM, EPROM, EEPROM), flash memory, CD-ROM, DVD, or other solid state memory technology, optical storage, magnetic storage devices, or any other medium which can be used to store the temperature information. For example, the controller may record temperature measurements to a memory card, which can then be accessed by the patient, physician, or other care provider to monitor or adjust therapy.

In cold therapy, it is important that the patient's skin temperature not get too hot or too cold. The target controlled temperature range for maintaining healthy tissue can vary among individuals due to physiological variability of vasculature, weight, health, type of injury, age, and other factors. A typical target temperature $T_2$ of the gas is 55° F., with a functional range of 45-65° F. In use, the controller has programming for an appropriately narrow range of temperatures that would be acceptable for patient skin, and the temperature measurements from the temperature sensor 132 are compared to that range. If the signal indicates a temperature below the lower limit of the range, the temperature of the gas being delivered to the therapy pad is preferably adjusted to be warmer. The gas is cooled if the signal indicated a patient temperature that exceeds the upper limit of the range. In preferred embodiments, the skin temperature is monitored, for example, by an IR diode, and the gas temperature, for example, $T_2$, is adjusted.

In preferred implementations, a safety mechanism is provided to disable the delivery of cold therapy gas if the skin temperature reaches a predetermined threshold indicative of hypothermia or other intolerable levels of skin temperature or cool air exposure. Similarly, if warm gas is being used, upper thresholds are provided that, if exceeded, could trigger a shutoff or reduction of the delivery of warm gas.

In certain embodiments, a safety mechanism is provided to limit therapy duration within safe limits. For example, the controller 130 may automatically stop therapy after predetermined therapy times, such as a 60 minute therapy session followed by automatic shutoff. The controller may calculate safe therapy durations based on the gas temperature and skin temperature during the therapy session and provide appropriate therapeutic interventions, including adjusting the gas temperature, or stopping therapy. In certain embodiments, the therapy may be provided in cycles, for example, 30 minute therapy sessions followed by 60 minute resting periods. In certain embodiments, for example, under physician supervision, therapy is provided continuously over extended periods up to 48-72 hours or longer as prescribed. Thus minimum, maximum, and target temperature ranges and therapy duration are all preferably programmed into the micro controller for controlling the temperature of the gas delivered to the therapy pad and, accordingly, the temperature of the skin at the patient. In certain embodiments, the safety mechanisms include recording the therapy parameters to storage media, such as flash memory, therapy parameters, may include, for example, duration of therapy, date and time of therapy, skin temperature, gas or fluid temperature, and the date and time of shutoff or other adjustment.

Figure 4B:
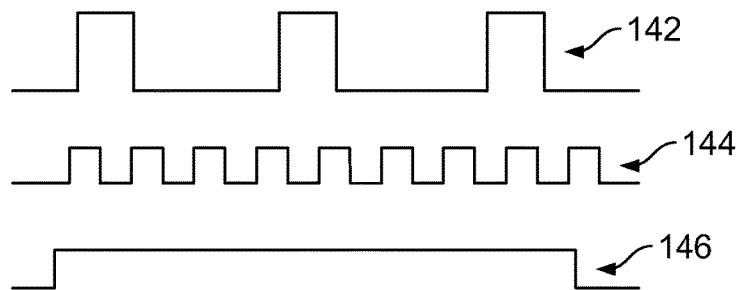

In use, as the controller senses the patient temperature and makes adjustments, the controller adjusts the magnitude, pulse width, or frequency (or a combination) of the current delivered to the Peltier device 121, thereby adjusting the temperature of the surfaces 118 and 121 and, in turn, adjusting the temperature $T_2$ of the gas that exits the temperature regulator 102. FIG. 4B shows different pulse frequency and pulse widths of example signals that could be delivered to the controller. For example, one pulse pattern is shown as signal 142. A higher frequency and lower pulse width is shown as signal 144. A low frequency, long pulse width is depicted as signal 146.

Figure 5:
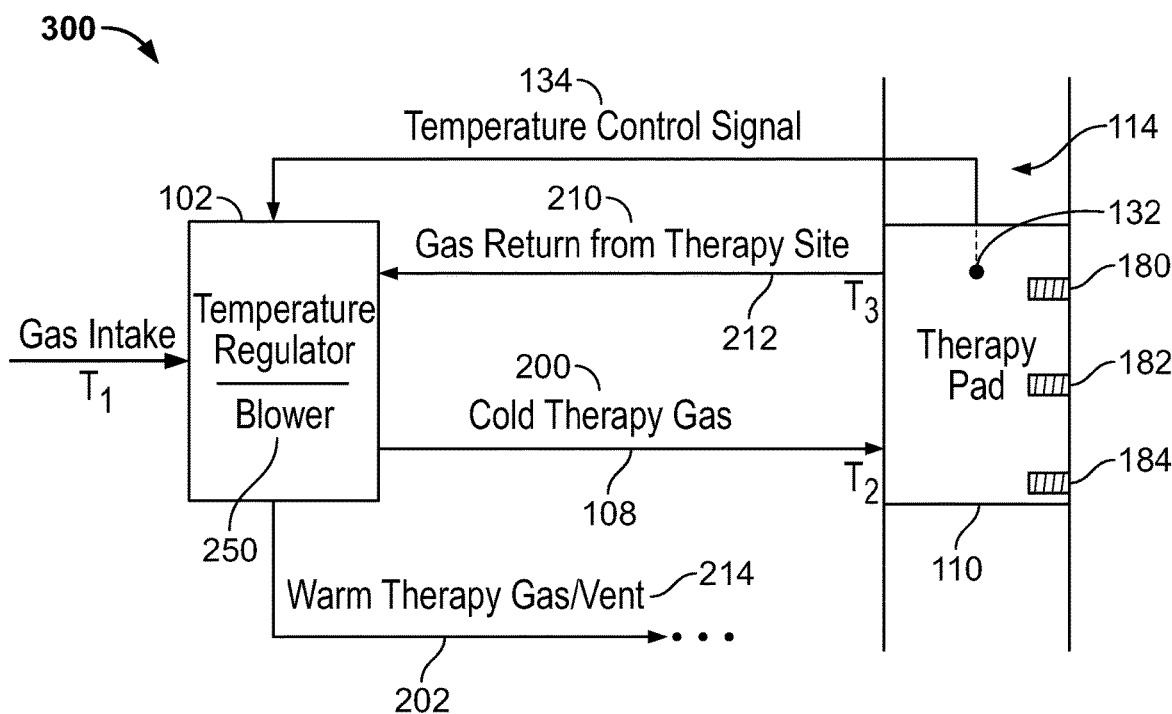
FIG. 5 depicts a therapy fluid temperature control system.

The temperature of the therapy gas delivered to the patient can be controlled by using warm or cold portions of the gas that is heated or cooled by the temperature control element 115 and by gas returning from the therapy site. FIG. 5 depicts a system 300 for controlling temperature at the therapy pad similar to the system 100 in FIG. 1. As shown, cold therapy gas 200 is delivered to the therapy pad by the tubing 108 at the temperature $T_2$. The gas flows through the therapy pad 110 (which is strapped onto the patient 114 via straps 180-184) and exits the therapy pad through the return line 212. The exiting gas 210 has warmed to a temperature $T_3$ because it passed through an injured site, which had been swollen and become hot because of the swelling and elevated temperature at the site. The warm gas $T_3$ flows back into the temperature regulator 102 and mixes with cold gas within the regulator and is then delivered back to the pad.

Also shown in FIG. 5, the temperature sensor 132 takes a temperature of the gas inside the pad or directly on the therapy site and sends the temperature control signal 134 back to the regulator 102 for adjustment of the cold therapy gas 200 temperature $T_2$ for delivery back to the pad 110. The warm therapy gas 214 can be either vented or delivered back to the patient at another location through venting line 202. In certain implementations, the warmed gas 214 is sent to a second therapy pad disposed at a different therapy site on the patient, for example about the torso or around the shoulders to capture the heat from the warm gas to warm the patient. In certain embodiments, cool therapy is provided to a first therapy site, such as the knee, while warm therapy is provided concurrently to a second therapy site, such as the lower back. For example, the first injury site may have swelling that can be aided by cooling, while the second injury site may have muscle tightness that can be aided by warming. Concurrent cooling and warming can also provide increased patient comfort during therapy sessions. For example, some patients find that cooling therapy at one therapy site is more tolerable when warming therapy is simultaneously provided at a second therapy site. In certain embodiments, the second pad is disposed on a different patient.

Also shown in FIG. 5 is a blower 250 which is preferably used to push the cold gas 200 through the system as well as push the warm gas 214 through the system. The blower may be a pump, fan, or other device to move a fluid. The blower intakes gas at temperature $T_1$ from the atmosphere (or tank or other source) and blows it across the temperature control element 115 (see FIGS. 2-4) and thereby moves the gas through the system. In certain embodiments, the blower speed, and thus the flow speed of the gas, is adjustable. Adjusting the flow speed of the gas provides an alternative or additional means of regulating the temperature at the therapy site. Increasing the flow speed increases the volume of air delivered and thus increases the heat carrying capacity of the system. In certain embodiments the velocity of the gas is between about 1 meters per second and 10 meters per second, and preferably about 3.5 meters per second. However, any appropriate velocity may be used for providing effective temperature control therapy at the target temperature. For example, a higher gas velocity may be used for larger injury sites or for sites with elevated temperatures.

Figure 6:
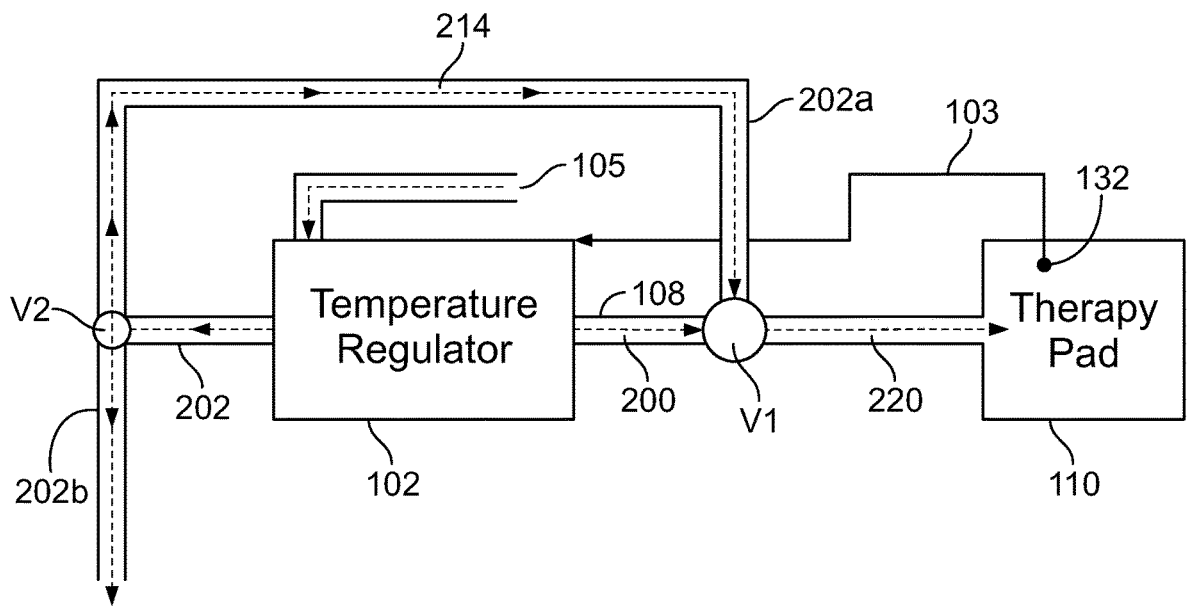
FIG. 6 depicts an alternative embodiment of a temperature control system, having heated air mixed with cold air.

An alternative temperature control system using fluid circulation and mixing is described in FIG. 6. As shown, the cold air 200 and warmed air 214 are mixed in mixing valve "V1" prior to delivery to the pad. The cold air 200 travels through line 108 from the internal cooling element and the heated air 214 travels through the heating element through the vent line 202 at valve "V2." The exiting warmed gas can split at valve "V2" and flow down line 202b, where it is vented, or along piping 202 and mixed at the valve "V1." The mixed air 220 is then delivered to the therapy pad 110 at the desired pad input temperature. The temperature regulator 102 can thereby adjust the temperature of the cold air 200 that is generated within the regulator, and can also modify that temperature downstream by the heated air 214 at the mixing valve "V1." This provides a supplementary process for adjusting the temperature of the fluid entering the pad. In some implementations, recirculating or mixing the heated air 214 with the cold air allows the user to more quickly adjust the temperature of the mixed air 220 to more appropriately suit the patient's temperature needs.

The system described herein provides air or other gas for temperature-controlled therapy to a patient, which can provide enhancements and advantages over existing technologies. As described above, the temperature controls are preferably performed by both thermal electric processes, such as through voltage changes across a conductive medium, and also by circulation controls, which allow fine tuning and quick adjustment of therapy fluid. In preferred implementations, the use of air or other gas-based fluids provides additional advantages that improve therapy provided to the patient. One advantage is that gas and air can be used in cooling systems that distribute the air or the gas directly onto the patient's therapy site, rather than requiring a fully insulated wrap, although closed loop systems with fully insulated wraps can be used. In certain implementations, the orthopedic wrap itself is configured to allow the therapy gas to flow directly upon the patient's tissue, thereby providing a potentially drier and more direct source of therapy control. In certain implementations, such a system allows the caregiver to integrate other therapy such as electrotherapy.

The systems and methods described herein, including systems 100 and 300, may also provide temperature-controlled therapy of other fluids, including liquids, such as water. The temperature of the liquid can be adjusted to temperature $T_2$ at the temperature regulator 102, delivered to the therapy pad through tubing 108, and returned to the temperature regulator 102 through tubing return line 212, where the temperature can be appropriately adjusted to target temperature $T_2$ and re-circulated. The temperature of the liquid may be further controlled using valves to direct mixing, as described in FIG. 6.

The closed-loop liquid system has advantages over conventional temperature-controlled therapy systems that use liquids. For example, conventional systems require use of a large reservoir of ice and cold water. The bucket can be awkward and heavy to transport, which can impair portability and mobility. Also, as the cold water circulates through the orthopedic wrap and along the patient's injury site, it warms and returns to the ice bath, where it melts the ice and ultimately raises the temperature of the bath. For long-term use, the ice must regularly be recharged and replaced in order to remain useful in managing swelling and temperature at the patient injury site. When the patient is under the supervision of a caretaker, such as a nurse, the caretaker must repeatedly add ice to maintain the proper cold therapy for patients. Additionally, the volume of water corresponding to melted ice must be removed. This regular maintenance adds physical strain to the patient or caregiver. It can also result in less effective therapy due to temperature variation or lapses in therapy until the ice is replaced.

System 300 provides temperature regulation through temperature regulator 102 that can heat or cool the gas or liquid directly to the target temperature $T_2$ without the need for ice. Accordingly, the system 300 utilizes a smaller reservoir and smaller volume of liquid, which reduces size and weight for improved portability and ease of use. In certain embodiments, the entire volume of liquid in the system 300 is continually circulated between the injury site and the temperature regulator such that no reservoir is used and a relatively small volume of liquid is used. For example, the system 300 may require less than 1000 milliliters (mL) of liquid, such as water, that circulates to provide temperature controlled therapy to an injury site. In certain embodiments, the volume of liquid in system 300 is dependent upon the size of the injury site 112 and the size of the pad (e.g., pad 110) used. For example, a smaller injury site 112 would use a smaller pad 110 and a smaller volume of water. In certain embodiments, system 300 may require less than 500 mL of liquid. In certain embodiments, system 300 may require less than 250 mL of liquid. In certain embodiments, system 300 uses both a liquid and a gas to provide temperature controlled therapy.

Figure 7A:
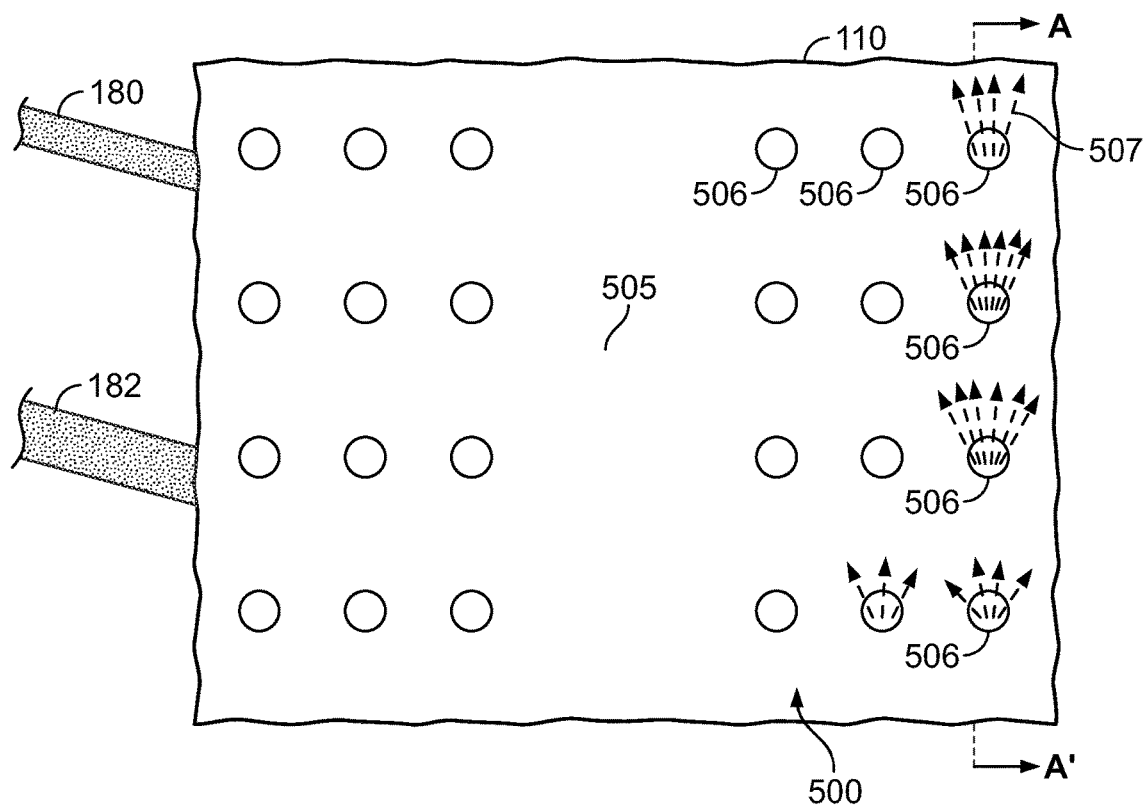
FIGS. 7A-7B depict an example of a therapy pad configured for use with air or gas-based therapy fluid system.
Figure 7B:
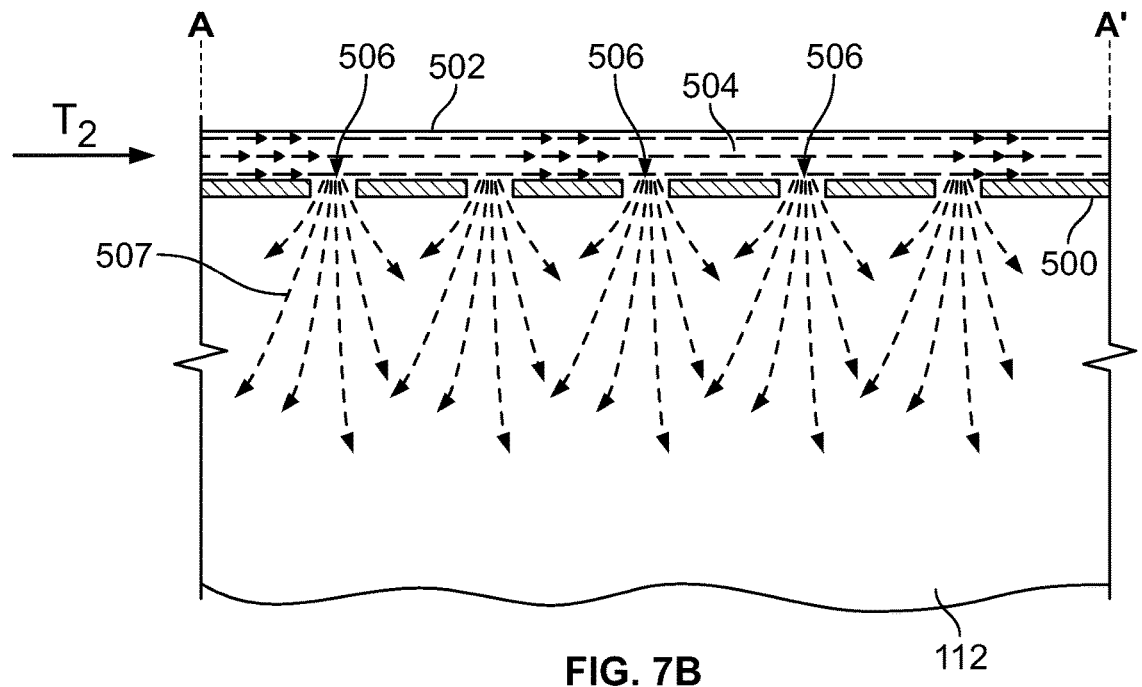

FIGS. 7A and 7B depict an example of a therapy pad configured for systems that provide cold therapy (or heating therapy) directly to the patient tissue. As shown, the orthopedic wrap 110 has an inner face 500, outer backing layer 502, support fold 505, and a flow channel 504 disposed between the inner face 500 and backing layer 502. FIG. 7B depicts a cross-sectional view of the wrap 110 shown along the line A-A'. As indicated, a plurality of holes 506 are disposed along the inner face 500 of the wrap 110. The holes allow gas 507 to flow from the temperature regulator (such as regulator 102 through gas line 108) and into contact with the patient's tissue at the injury site 112. The wrap 110 is held to the patient, for example, with support fold 505 around the patient's knee, by a plurality of straps 180 and 182. As shown in FIG. 7B, gas at a therapy temperature $T_2$ flows into the fluid channel 504 from the gas line 108 and, as it travels through the channel, exits at the various holes 506, providing temperature-controlled gas 507 directly to the patient therapy site. This allows for more rapid cooling of the patient than is done by closed systems that require changing the wrap's surface temperature before being able to cool the patient.

Figure 8A:
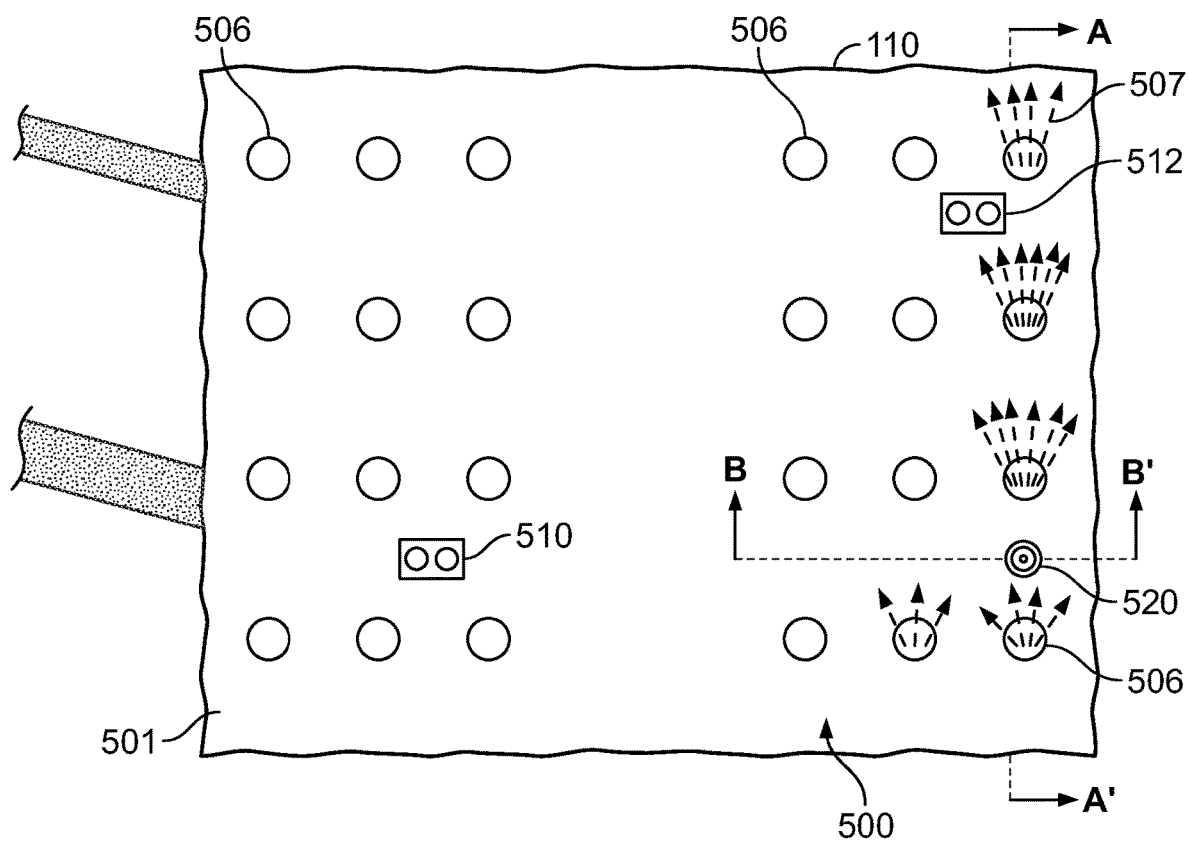
FIGS. 8A-8C depict an example of a therapy pad configured for use with a gas or air-based fluid therapy in combination with an electrical stimulation system.
Figure 8B:
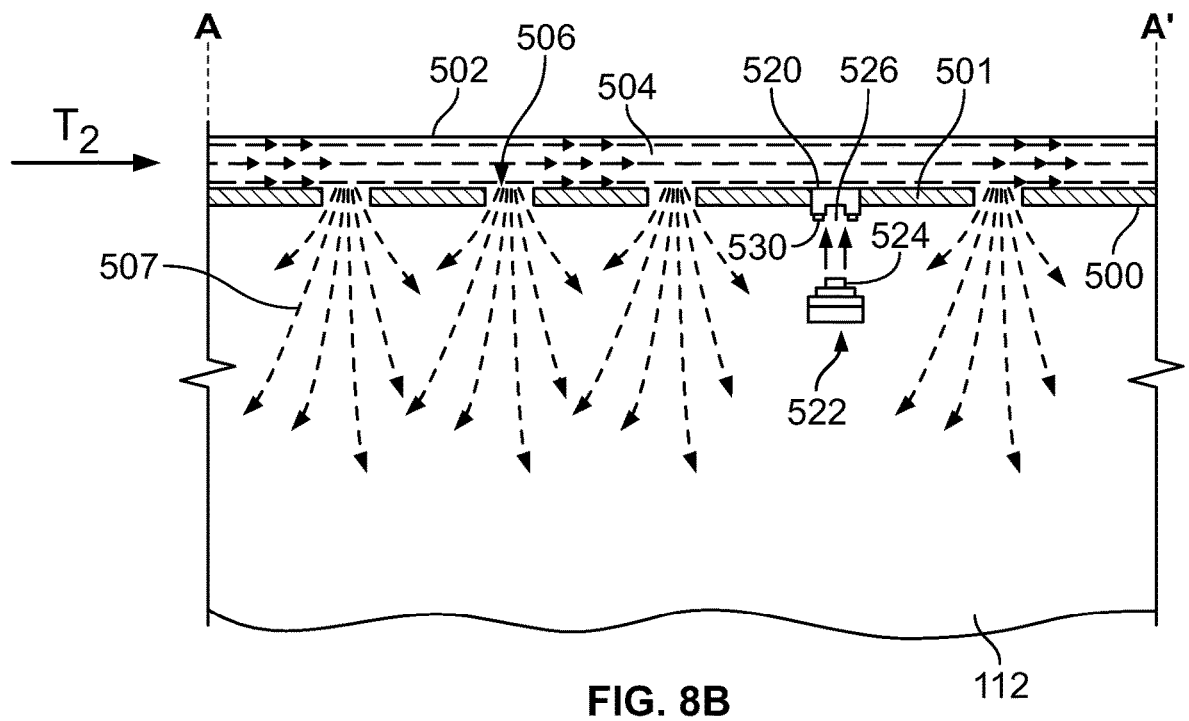
Figure 8C:
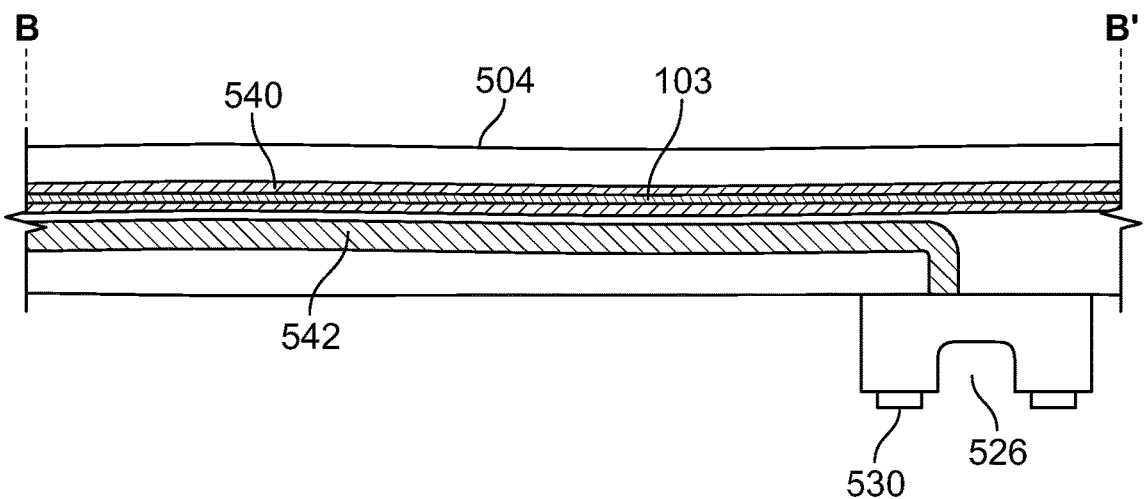

As indicated above, the wrap 110 with the one or more holes 506 disposed along the inner face 500 can be configured to receive and attach one or more electrodes for providing electro-stimulation (e.g., current, voltage) or other therapy to the patient in combination with temperature-controlled gas therapy. FIGS. 8A-8C depict an example of the wrap 110 of FIG. 7A-7B configured with electrodes disposed along the inner face 500 of the wrap. As shown, two electrode pairs 510 and 512, respectively, are mounted on the inner face 500. Those electrode pairs connect to an electro-stimulation unit by wiring disposed within the walls of the wrap 110. As shown, the electrodes are mounted by male and female snap electrode connections (but other techniques can be envisioned). In particular, a female connector 520 is mounted on the inner face 500 and configured to receive a male electrode snap 522. The male snap 522 has a button 524 that fits within the receptacle 526 of the housing 530 of the female connector 520. When the electrode is connected to the wall by the snaps, electrical stimulation can be provided to the injury site 112. At that same time, temperature-controlled therapy gas 507 (which can be heated or cooled) at temperature $T_2$ flows through the flow channel 504 and is expelled out of the holes 506. As the gas 507 flows out of the holes and onto the tissue site 112 it will contact and surround the electrode male snap 522, without corroding the snap 522, as may otherwise occur if water or other liquids were used as the coolant. The flow and circulation of the gas prevents condensation at the electrode, pad, and skin. The cool gas is preferably dry, and therefore can be applied in combination with electrical stimulation to the patient without corroding or rusting the electrode, or shorting electrical components.

The flow channel 504 is also structured to allow temperature-controlled gas to flow behind the female connector housing 530 without corroding that component. In particular, the female connector housing 530 is sewn or glued into the wall 501 of the inner face 500 of the wrap, and is stabilized within that wall, with the temperature-controlled gas flowing behind it and remaining within the channel 504.

As the orthopedic wrap 110 is configured to provide both mechanical and electrical based therapies, the wrap layers 500 and 502 are configured with insulated cabling that allows electrical conducting lines to pass from the electrodes or temperature sensors and out to the control mechanisms of the system. FIG. 8C is a cross-sectional view of the wrap 110 taken along line B-B' which shows insulated cable 540 extending in parallel with the insulated Cable 542. Cables 540, 542 are both disposed within the flow channel 504. Other configurations may also be used, for example, the cabling may be stitched or configured above or below the flow channel 504 to further isolate the cabling from the flowing gas. As shown, the insulated cable 540 houses temperature control signal line 103, and the insulated cable 542 houses an electrical line that extends from the connector housing 530 of the electro-stimulation electrode and out to an electro-stimulation controller located outside the wrap.

Figure 9:
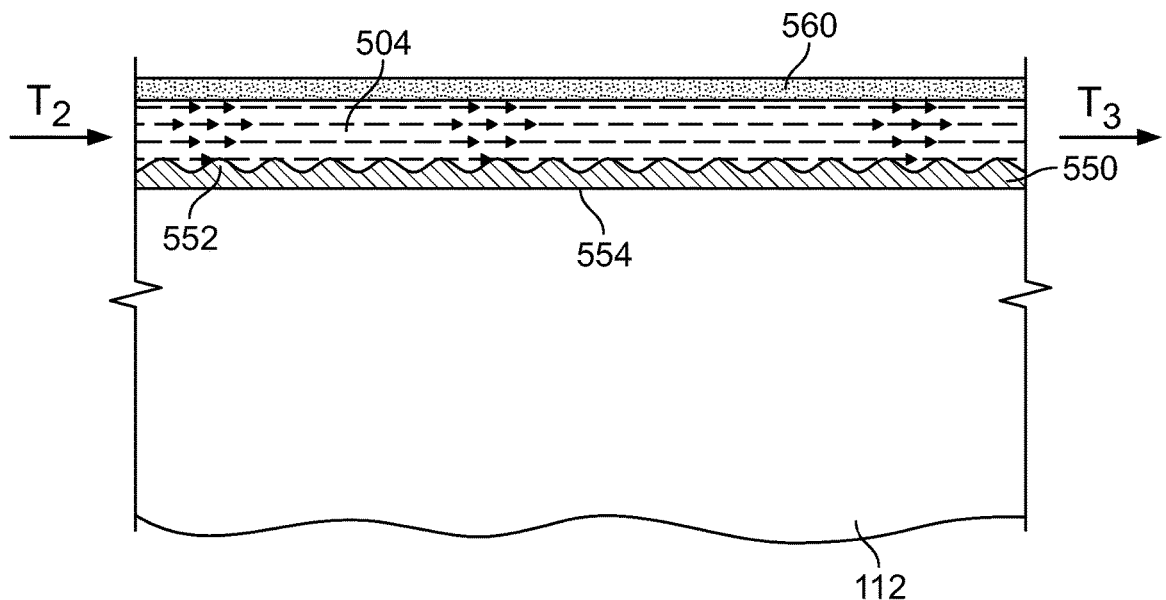
FIG. 9 depicts an example of a therapy pad configured for transferring heat to or from an injury site.

As depicted in FIG. 9, in certain embodiments, the heat is transferred between the therapy site and the gas through a heat exchange layer, but the gas is not delivered directly to the therapy site. Heat exchange without air flow to the injury site may be desirable if the gas can cause irritation or desiccation of the site. Flow channel 504 has a heat exchange layer 550, with a surface 554 that couples to the injury site 112, and an insulation layer 560. As the gas at temperature $T_2$ flows through flow channel 504, heat from the therapy site 112 is transferred across the heat exchange layer 550, thereby reducing the temperature of the injury site 112 and raising temperature of the gas to $T_3$. The gas carries heat away without blowing directly on the injury site. In alternative embodiments, a temperature-controlled liquid, such as water, flows through channel 508 and exchanges heat across layer 550 with the injury site 112 to provide cooling or warming therapy without delivery the liquid directly to the injury site 112.

The heat exchange layer 550 is constructed of a material with sufficiently high thermal conductivity (e.g., greater than about 0.1 watts per meter kelvin or "W/m-K") to allow heat flow between the injury site and the gas. For example, the heat exchange layer 550 may be foil, Mylar, composite, or any other suitable material. In certain embodiments heat exchange layer 550 includes texturing or other structures, such as ribs 552, to increase the surface area of the heat exchange layer 550 and thereby increase the exchange of heat between the injury site and the gas. The insulation layer 560 acts as a thermal conductive barrier and reduces heat exchange between the external environment and the gas to improve heat exchange efficiency at the therapy site and is typically composed of a material with low thermal conductivity (e.g., less than about 0.1 W/m-K). In certain embodiments the insulation layer 560 is polyurethane. Alternatively, materials with a high specific heat capacity (e.g., greater than about 2000 joules per kilogram kelvin or J/Kg-K) may be used as a fluid conductive barrier. For example, the insulation layer 560 may include propylene glycol.

Figure 10:
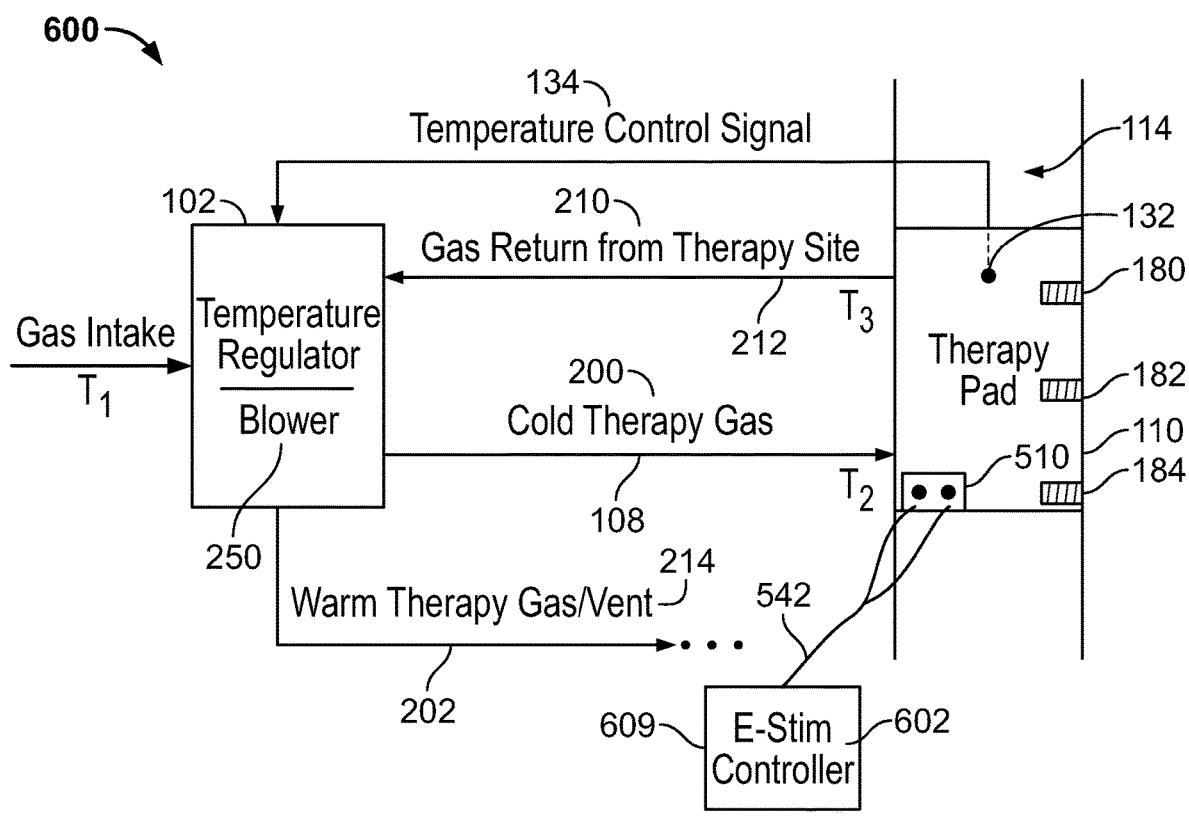
FIG. 10 depicts a system for providing temperature control therapy to a patient in combination with electrical stimulation.

FIG. 10 depicts a system 600 configured to provide temperature-controlled therapy to a patient in combination with electro-stimulation therapy. The system 600 is similar to the system 300 shown in FIG. 5 (and has similar components to the other systems described herein) with an added electro-stimulation ("e-stim") unit 602. In particular, the electro-stimulation unit 602 has a controller 609, connected to a plurality of electrodes 510 by an electrical conducting line 542. For example, the electro-stimulation unit 602 and controller 609 may be similar to the Empi Select 1.5, SportX, 300PV, IF3Wave, or Active stimulation units produced by DJO, LLC. As described above, the conducting line 542 can be disposed in insulating cabling within the flow channel of the therapy pad, as shown in FIG. 8C. In operation, the user can control the temperature of the cold therapy gas 200 flowing through the inlet line 108 by operation of the temperature regulator 102 and at the same time can control the parameters (current, voltage, magnitude, frequency, waveform, power, etc.) of electro-stimulation therapy provided to the therapy pad by the electro-stimulation controller 602.

Figure 11A:
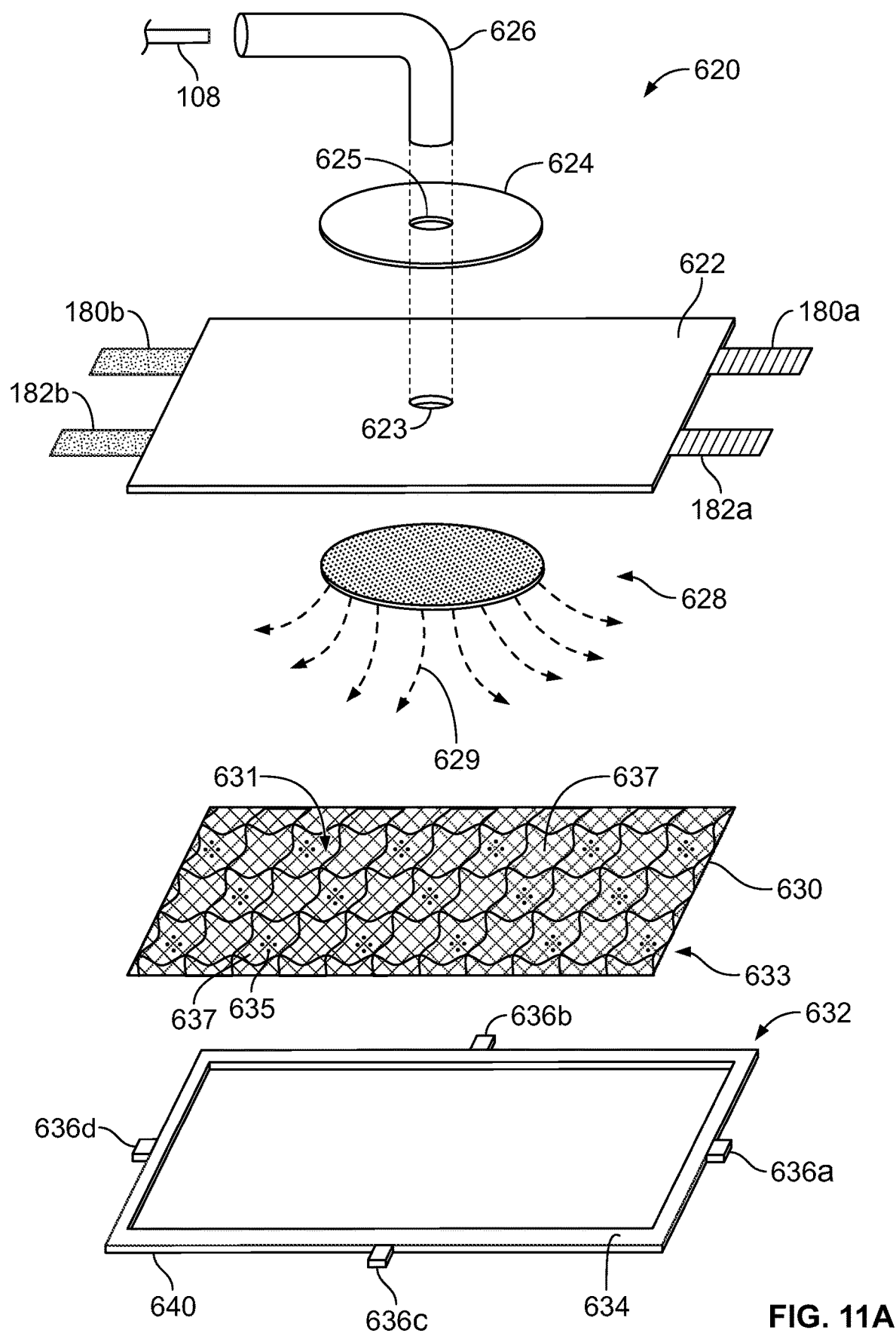
FIGS. 11A-11C depict an example of a therapy wrap configured for use with a gas coolant-based system.

While the orthopedic wraps with holes on the interface provide direct contact between the patient and the cooling or heating fluid, other implementations of the pad may also be used. FIG. 11A depicts an exploded view of an alternative thermal therapy pad 620 configured for use in a gas coolant-based system, such as those described above. As shown, the wrap 620 includes an insulated layer 622 on an upper end and a lower frame 632 having a channel 634 with a series of gas relief valves 636a-636d disposed about the channel 634 perimeter. A mesh layer 630 is placed between the insulated layer 622 and the lower frame 632 to provide a cushioning or 'standoff layer' with respect to the patient to allow adequate flow of the delivered gas around the therapy site. The mesh has a perforated diffusion plate 628 disposed between the upper surface 631 of the mesh layer 630 and the insulated layer 622. The perforated diffusion plate 628 is overlayed by a connecting ring 624. The connector ring joins to a foam joint tube 626 that receives a distal end of the flow tube 108 coming from the temperature regulator.

In operation, temperature-controlled gas flows through the tube 108 and into the foam joint tube 626, through the hole 625 disposed in the middle of the connector ring 624, and then through the hole 623 in the insulated layer and onto the diffusion plate 628. When the gas contacts the diffusion plate 628 it disburses laterally as shown by the arrows 629 so that it spreads across the upper surface 631 of the mesh layer 630 and substantially equalizes the pressure of the delivered gas. The mesh layer 630 is formed preferably in an eggshell or egg crate shaped structure having a plurality of dense undulations 637 that allow the gas to flow up and down and around the contours of the upper surface 631. In certain embodiments, a plurality of apertures 635 are disposed within the undulations 637, preferably in the bottom well of one or more of the undulations 637. The gas flows through the mesh layer 630 and onto the channels 634 of the lower frame 632, ultimately purging through the relief valves 636a-636d. As the gas travels within the mesh layer 630, it cools the lower surface 633 of the mesh layer 630 opposite the upper face 631 to provide cooling for the patient. The mesh 630 can also be structured to allow the intake gas to flow through lower surface 633 and thereby directly cool the patient's skin and vent through the relief valves 636. Heating can also be applied by simply reversing the polarity on the heating element 115, such as Peltier device 121 or otherwise providing a heat source or source of warm gas.

The insulated layer 622 is a soft polymer or other flexible material, such as rubber, polyethylene, or other suitable material. The connector ring 624 is preferably a polymer or thin metal and is positioned under the foam joint 626 to support the joint 626. A distal end of the joint 626 extends through the holes 625 and 623 to connect the joint 626 to the layer 622 and ring 624 for proper positioning with respect to the diffusion plate.

The perforated diffusion plate 628 has a plurality of holes and is therefore breathable. It is constructed preferably from a perforated polymer or thin metal material. In certain implementations, it is constructed of polyethylene or polyester and is about 0.5 to about 5 millimeters thick, preferably about 1 mm-2 mm. In certain embodiments, the mesh layer 630 has an eggshell surface and is foam. In alternative embodiments, the mesh layer 630 is a wire mesh. The lower frame 632 has a gasket 640 around its perimeter which helps affix the lower frame 632 to the patient. This gasket 640 is preferably constructed of soft polymer that holds the wrap in place and also holds in place an electrode that may be connected to the lower face of the frame or the mesh layer. In certain embodiments, the polymer is adhesive. In this respect, the gasket can help eliminate the need for a hydrogel or glycerol gel for attaching a electrode, as the overall wrap itself will be sticky enough and strong enough to align the wrap on the patient and therefore align the electrode in its proper position. For example, the electrode could be sewn or stitched into the wire mesh or into the lower frame, as shown in FIGS. 8A-8C.

Figure 11B:
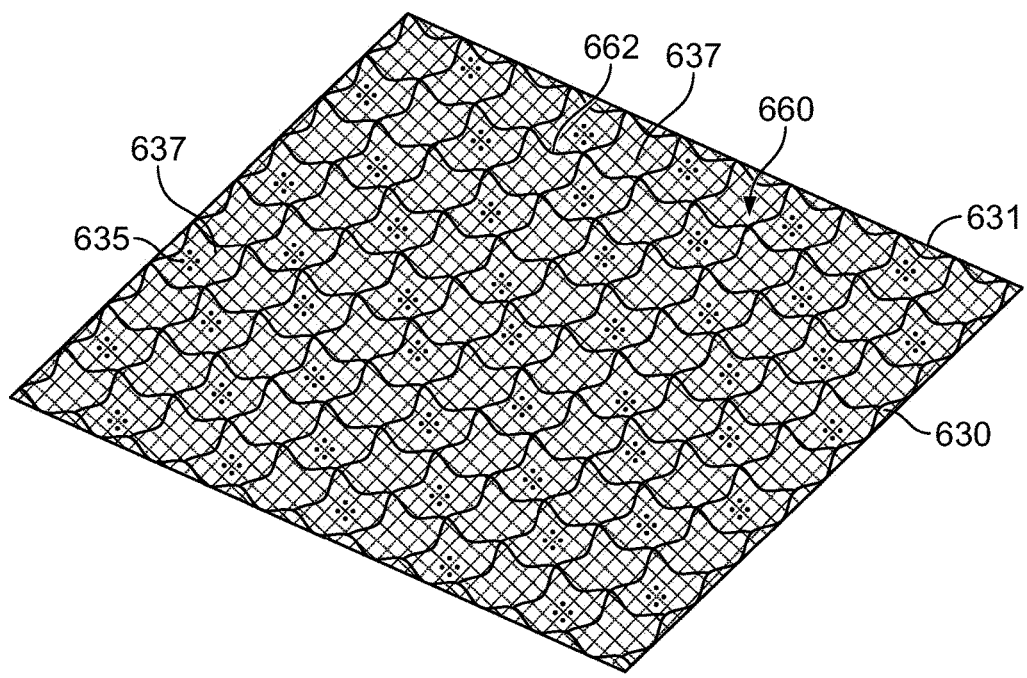
Figure 11C:
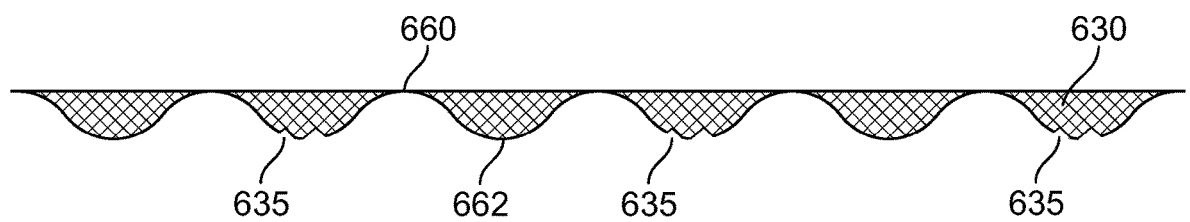

The mesh layer 630 is shown in further detail in FIG. 11B and FIG. 11C. FIG. 11B depicts a top view of the upper surface 631. The undulations 637 include a plurality of indent depression structures 660 surrounded by a plurality of ridges 662. Apertures 635 are depicted on the ridges 662, but may be disposed on any part of the mesh layer 630. FIG. 11C depicts the ridges 662 and depressions 660 in cross section. In preferred implementations, the mesh layer 630 is constructed of an open cell foam having a plurality of apertures or may be made of tightly meshed wire or other material. The ridges 662 and depressions 660 can include gaps or spacings between them, as in the case of a wire mesh, to allow therapy gas to flow through and reach the patient.

Figure 12A:
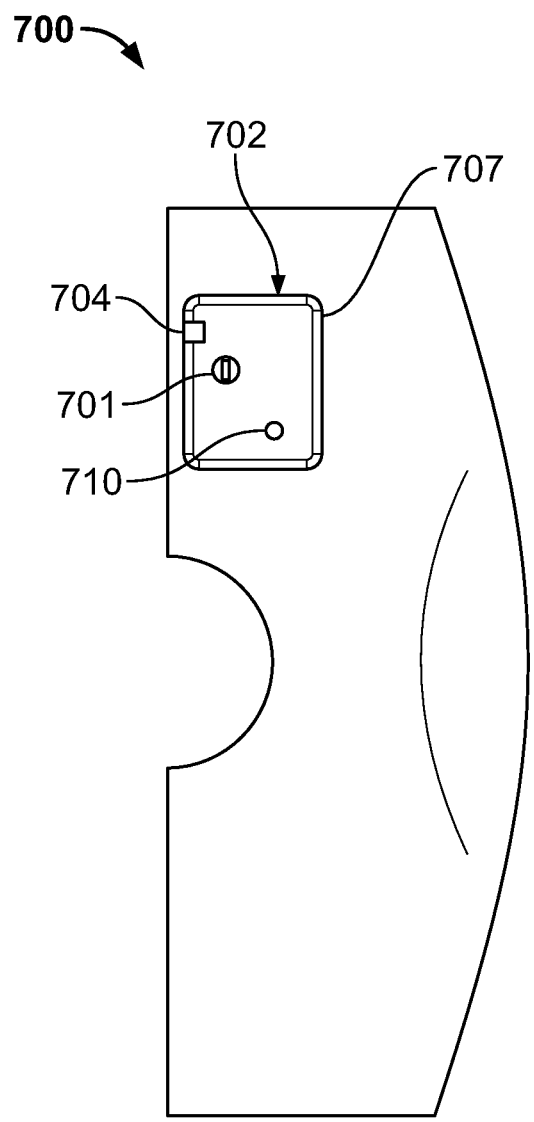
FIGS. 12A-12C depict an on-board therapy control system that combines electrical stimulation with fluid therapy that is temperature-controlled.
Figure 12B:
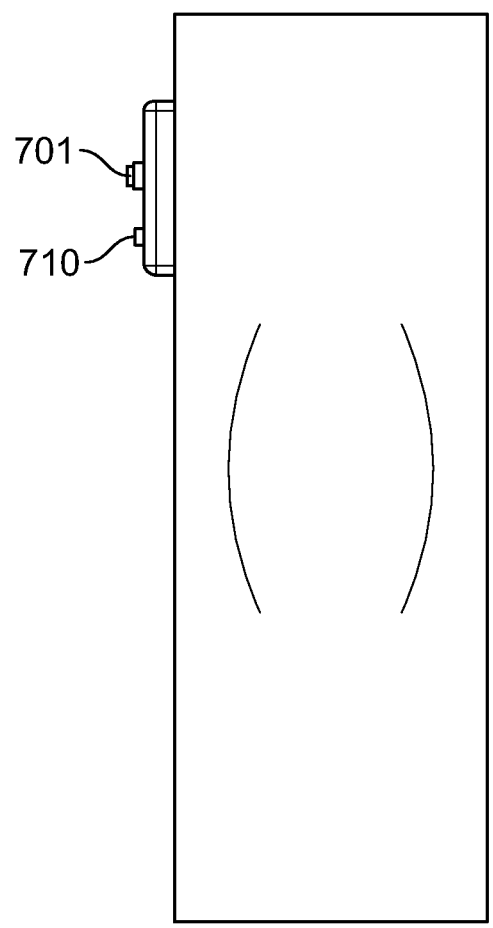
Figure 12C:
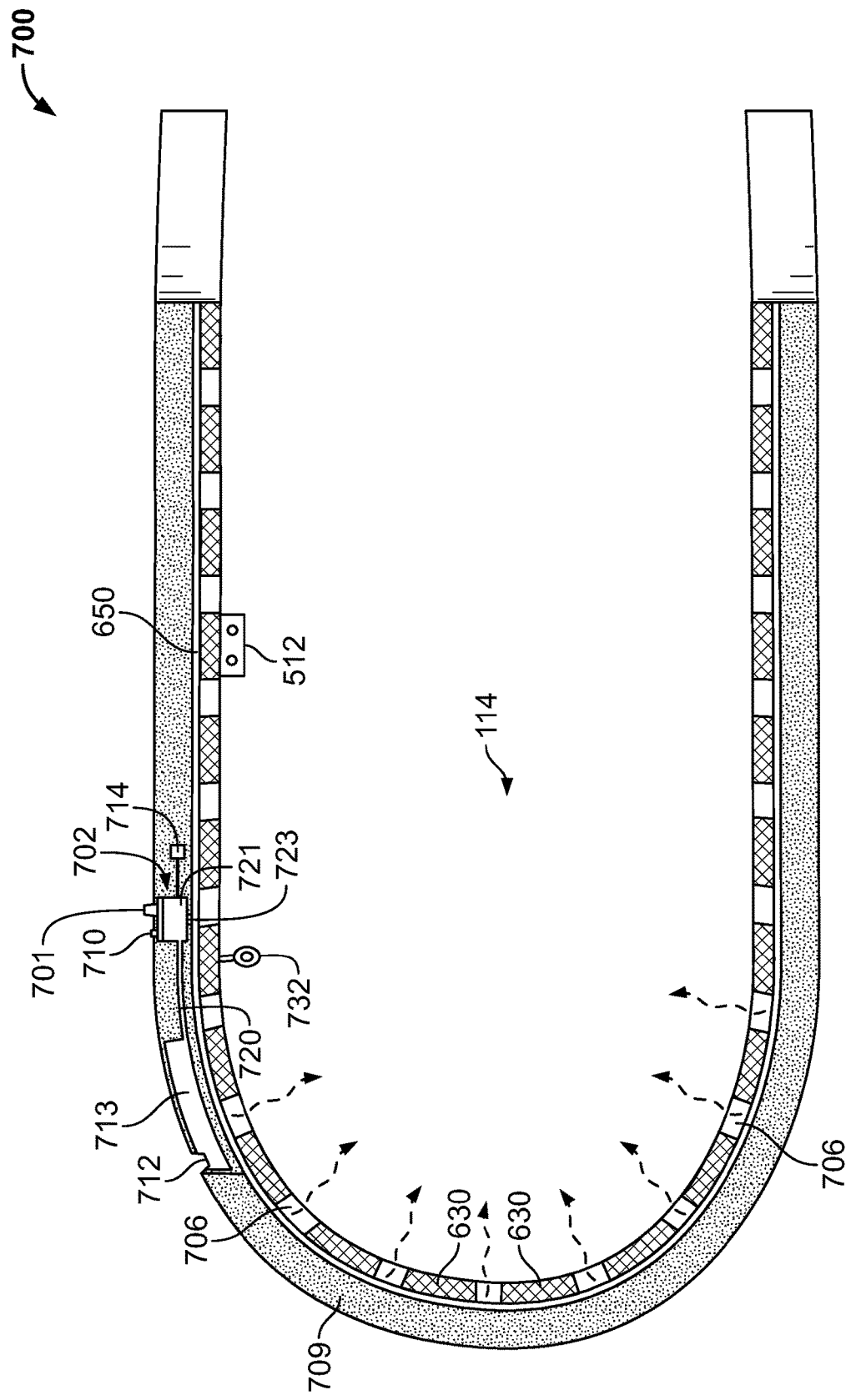

The therapy temperature control systems described above can be modified for improved patient handling and use, with lower profile and fully on-board implementations. FIGS. 12A-12C depict an example of a therapy wrap housing with a fully on-board temperature control regulator used to cool or heat patient tissue. FIG. 12A shows a side view of a knee wrap 700 and FIG. 12B shows the front view of that knee wrap. As shown, a knee wrap 700 (which is similar to the orthopedic wrap system 100 described above) includes an on-board temperature control regulator 702 that receives gas, such as ambient air or stored gas, through an intake port 704 and adjusts its temperature by actuating a control knob 701. The gas intake and temperature control components are loaded within the housing 707, which is self-contained and self-powered, so the patient can provide cold or warm therapy without needing to carry a large ice bath or other cumbersome source of energy or cooling fluid. An electrode actuator 710 is optionally also included, and the wrap 700 is configured inside the wrap with an electrode, similar to those discussed above. FIG. 12C shows that the knee wrap 700 in cross section from the inside, with the temperature control regulator 702 fully on board and loaded within the layers of the wrap itself. As shown, the temperature regulator 702 is sewn or stitched within an outer layer 709 of the wrap and delivers gas to the inner mesh layer 630. In certain embodiments, the outer layer 709 has top and bottom surfaces and a thickness, and is constructed substantially of foam. The regulator 702 includes both an intake manifold 712 and a blower 713 for receiving and pumping ambient air through the system. The intake ambient air passes through an inner tube 720 that is also disposed within the outer layer 709, providing fluid communication to the heating/cooling chamber 721 which is equipped with a heating or cooling element (or both) and a fan. For example, the element 721 could be similar to heating/cooling element 115 described above. The temperature of the air is adjusted within the chamber 721. It then passes out of the chamber and through an outlet hole or port 723 in the outer layer 709 and into the flow channel 650, similar to channel 504 within the wall of the wrap. The air then passes through the plurality of apertures 706 in the mesh layer 630 and into the inner area 114 of the wrap, where it can contact the tissue of the patient. The temperature control of the fluid within the chamber 720 is adjusted by the knob 701.

Also shown, a plurality of electrodes 512 are configured on the inner face of the mesh layer 630 (or otherwise in the inner face of the wrap 700) and can be adjusted to provide therapeutic electro-stimulation by operation of the electrode actuator 710. A battery 714 is also loaded within the control unit 702 to provide an on-board power source for operating the blower, the temperature control, and the electrode stimulation current control. This structure thus provides a fully on-board, easy to use and low profile control system that allows the patient to receive both temperature-controlled therapy and electrode therapy, including electrical stimulation, to address both surface and deep tissue pain. Examples of appropriate batteries for this operation can include 12V lantern batteries with at least 5000 milliampere-hours (mAh) of charge. Rechargeable batteries, including, but not limited to, nickel metal-hydride, lithium polymer, and lead acid batteries in commercially available or custom forms may also be used.

Figure 13A:
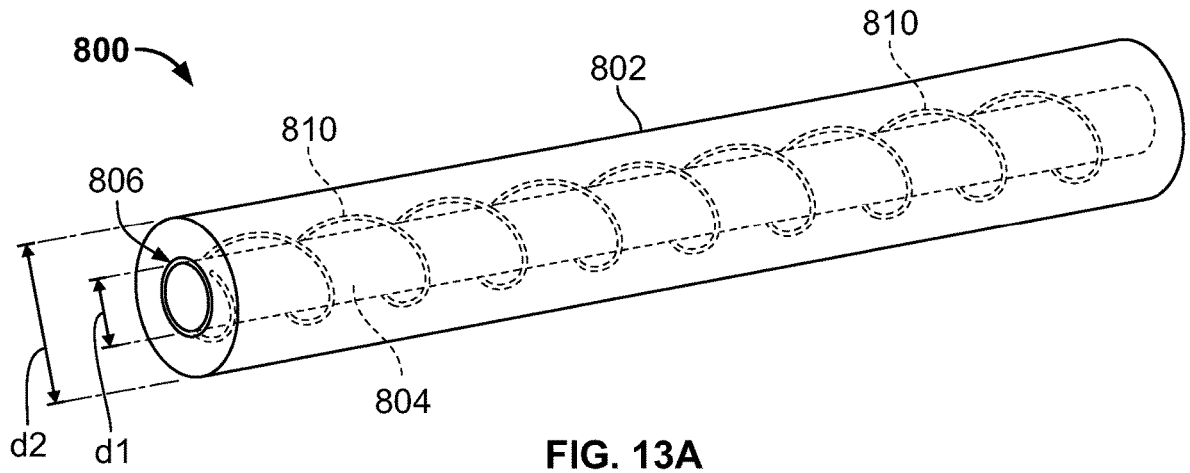
FIGS. 13A-13B depict flow tubing configured to enhance thermal efficiency of therapy gas in a temperature-controlled therapy setting.
Figure 13B:
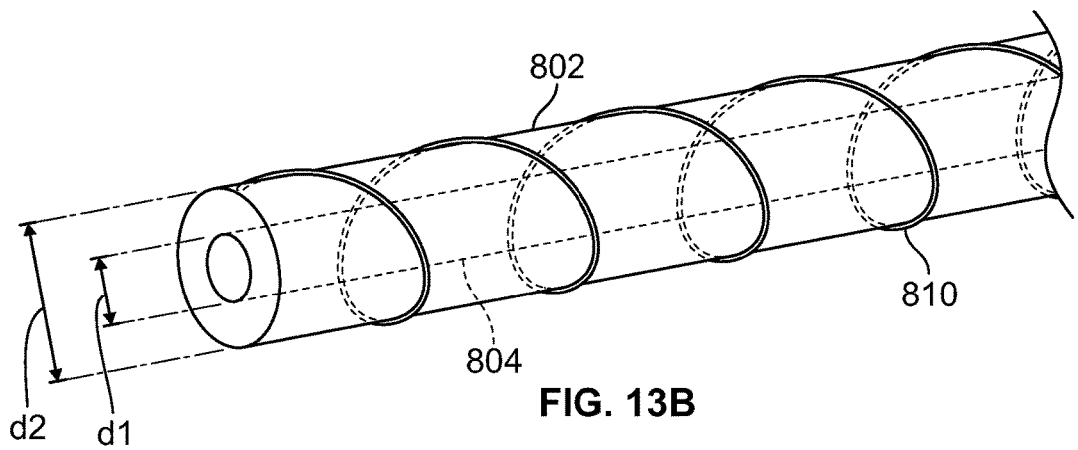

In certain implementations, improved insulated piping and flow structures are also included. FIGS. 13A-13B depict an example of a flow tube 800 that can be used, for example, as the air flow line 108 of the examples shown above. This flow tube 800 is preferably made of foam or other insulated material, and it has an outer foam or other insulated surface 802 with an inner flow tube i 804. The inner flow tube 804 preferably has an inner foam surface 806 that contacts the gas or air as it flows through the tube 800. In certain implementations, the tube 800 may have a tendency to buckle or kink and thereby impair the system's cooling or heating functionality. FIG. 13A addresses this by providing a self-expandable inner coil 810 coaxially disposed within the walls between the outer foam surface 802 and the inner flow tube of 804 of tube 800. The coil 810 can be made of Nitinol wire, or other recoilable and expandable material that is self-expandable and yet can retain its position under stress. The coil 810 is preferably co-extruded within the tube 800 so that it is disposed within the walls of the tube. Alternatively, the coil 810 can be disposed around the outside surface 802, as shown in FIG. 13B.

The inner flow tube 804 has a flow diameter "d1" that is wide enough to allow high pressure air or other gas to flow through the tube. The flow tube surface 806 may be substantially smooth to provide adequate air flow. In certain embodiments, the diameter "d1" may be between about 0.25 and about 0.75 inches, and the outer surface may be between about 0.25 and about 2 inches, to provide an outer diameter "d2" between about 0.5 and 2.75 inches, preferably between about 0.375 and 0.75 inches. However, any appropriate diameters "d1" and "d2" may be used for adequate air flow and thermal insulation. For example, large therapy pads or a plurality of therapy pads may required larger tubing for increased air flow.

Figure 14:
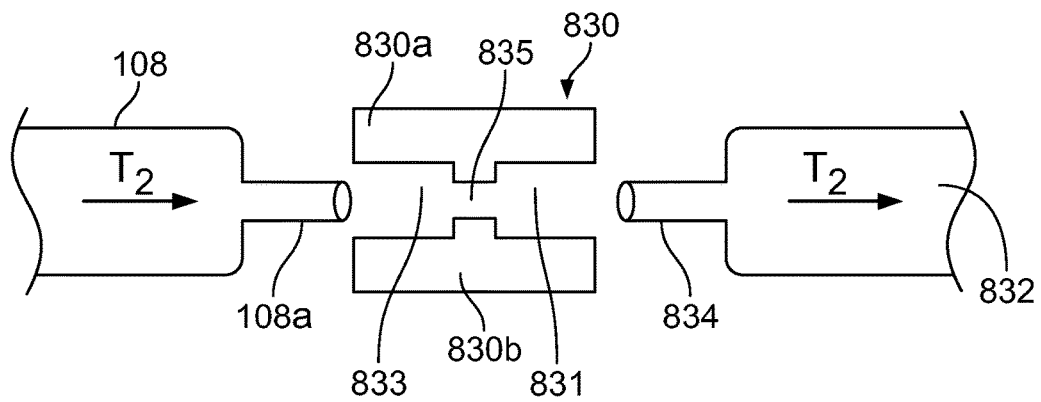
FIG. 14 depicts couplings for tubing used in a temperature-controlled therapy system.

Additional insulated structures can also be used to help to conserve energy and maintain the therapy gas at the desired temperature. FIG. 14 depicts an example of a coupling mechanism that can be used to provide insulation around the connection between the therapy fluid delivery tube 108 and the therapy pad, or between the exit of the temperature regulator and the entrance to the delivery tube 108. As shown, a foam coupling 830 includes an upper wall 830a and a lower wall 830b, with a first female inner receptacle 831 and a second female receptacle 833 structured as apertures. A narrowed passageway 835 is disposed between the two receptacles within the coupling 830. The first receptacle 831 receives a male connector end on the line to the therapy pad. The connector end 834 of tube 832 fits within the female receptacle 831 by a friction fit. Preferably, the connector end 834 is also made of foam and, therefore, the foam of the inner walls of the receptacle 831 can connect by friction and stay together with respect to the connector end 834. A similar structure is used on the opposite side of the coupling, where female receptacle with foam walls 833 receives the foam connector end 108a from the flow tube 108. The passageway 835 is a narrowing in the flow channel between the upper 830a and lower 830b foam walls, and has a diameter that is smaller than the diameters of either of receptacles 831 or 833, respectively. In practice, the tube 108, tube 832, and coupling 830 are thermal insulators that enhance thermal efficiencies of the flow circuit by reducing external heat transfer. Tube 108, tube 832, and coupling 830 may be insulated foam, and could be substantially the same foam. For example, tube 108, tube 832, and coupling 830 may be constructed of a foam material having a thermal conductivity no greater than about 0.08 W/m-K, and preferably less than about 0.5 W/m-K. In use, the extensions 108a and 834 are inserted within their respective female receptacles, 831 and 833, and are thereby held together by a friction or interference fit. Temperature-controlled gas is thereby delivered through the tube 108 passing through the foam connector ends 108a through the passageway 835 and into the therapy pad. In certain embodiments, the coupling may be integrally provided with the tube 108 or tube 832.

The systems and methods described herein may be integrated with garments to provide temperature regulating garments worn by patients. FIG. 15 depicts an example garment 940 that can be worn on the legs of a patient. The garment 940 includes at least one pocket 944 for retaining one or more therapy pads, such as therapy pad 110, disposed within an outer shell 942. The garment 940 depicted in FIG. 15 includes a plurality of pockets 944a-d. In certain embodiments, the shell 942 is constructed of a compressive fabric, such as spandex, nylon, polyester, or latex, to provide compression to the injury site and more securely retain the therapy pad.

The shell 942 of the garment 940 forms at least one sleeve 946 structured to wrap around the patient anatomy having an injury site, such as a leg, arm, shoulder, back, or chest. The garment 940 depicted includes a plurality of sleeves 946a and 946b. The garment 940 also has an inner area 941, formed by an inner boundary of the sleeve 946, that receives the patent's body. The at least one pocket 944 is preferably located near or directly on an injury site, such as injury site 112 of patient 114, and can be structured with an interior webbing, netting, or other porous passageway that interfaces with the pad and allows the gas flowing through the pad 110 to pass through the inner garment wall and into the inner area 941 of the garment 940, where the gas contacts the injury site to help facilitate temperature regulation of the injury site. In certain implementations, the location for placing the pockets 944 on the garment is customized to the patient and can be determined by the location and size of the injury site.

The garment 940 can be configured to deliver gas directly to the injury site, as previously described. For example, pad 110 may include at least one hole 506 as depicted in FIGS. 7A-7C and FIGS. 8A-8C or aperture 706 as depicted in FIGS. 12A-12C. At least one hole or aperture may be located in the sleeve 946. In certain embodiments, the garment 940 is configured to transfer heat between the injury site and the gas across a heat exchange layer, such as layer 550, as depicted in FIG. 9.

In certain embodiments, the pad 110 is formed as an integrated, self-contained temperature control device, having a cold or hot air generation source (for example, a Peltier coil or other examples discussed herein) that can be placed inside the pocket 944. For example, a Peltier-containing housing can be glued or stitched to a pad, such as pad 110, to create a single, hand-held device. The pad is then placed in the pocket and, when activated, blows cold (or hot) air through the pocket interior surface and onto the patient.

FIG. 16 shows a garment 900 with an integrated flow channel 904 within the garment shell 902. At least one flow channel 904 is shown, and in some embodiments, a plurality of flow channels are used. In certain embodiments, the shell 902 is constructed of a compressive fabric, such as spandex, nylon, polyester, or latex, to provide compression to the injury site.

The shell 902 of the garment 900 forms at least one sleeve 910, as depicted sleeves 910a and 910b, structured to wrap around the patient anatomy having an injury site, such as a leg, arm, shoulder, back, or chest. In operation, the gas at temperature $T_2$ enters the channel at entry end 906 and flows through the tubing in channel 904, thereby adjusting the temperature of the injury site. For example, the flow channel 904 may include at least one hole 506 as depicted in FIGS. 7A-7C and FIGS. 8A-8C or aperture 706 as depicted in FIGS. 12A-12C to deliver gas directly to the injury site. In certain embodiments, the hole or aperture is located in the sleeve 910. In certain implementations, the placement of the holes or apertures is customized to the patient and determined by the location and size of the injury site. In certain embodiments, the flow channel 904 includes a heat exchange layer, such as layer 550, depicted in FIG. 9 to transfer heat between the injury site and the gas. The gas flows through the circuit path and then is released through exit port 908 at temperature $T_3$. In certain embodiments, the gas is pressurized, for example, by blower 250, to provide compression.

FIG. 17 depicts a garment 920 with at least one integrated temperature regulator 924, which is similar to temperature regulator 102 shown in FIGS. 1 and 2. The garment 920 includes a plurality of regulators 924. In certain embodiments, the temperature regulator 924 includes a thermoelectric generator, such as the Peltier device 121 depicted in FIG. 3A. A cable 929 connects the temperature regulator 924 to a power source, such as a battery or outlet. In certain embodiments, the temperature regulator 924 is powered by an integrated battery.

In practice, the temperature regulator 924 provides heating or cooling near the injury site for efficient temperature regulation. In certain implementations, the location of the temperature regulator 924 is customized to the patient and determined by the location and size of the injury site. In certain embodiments, the target temperature of each regulator is adjusted independently of other regulators. The temperature regulators 924 may be flexible in structure to accommodate the contours of the patient.

In practice, the garment 920 includes an outer fabric or shell 922. In certain embodiments, the shell 922 is constructed of a compressive fabric, such as spandex, nylon, polyester, or latex, to provide compression to the injury site. The shell 922 of the garment 920 forms at least one sleeve 926, as depicted sleeves 926a and 926b, structured to wrap around the patient anatomy having an injury site, such as a leg, arm, shoulder, back, or chest. Temperature-controlled gas may be delivered directly within the sleeve 926 to the injury site through at least one hole or aperture, as previously described, for example in FIGS. 7A-7C, FIGS. 8A-8C, and FIGS. 12A-12C. In certain implementations, the placement of the holes or apertures is customized to the patient and determined by the location and size of the injury site. In certain implementations, heat is transferred between the injury site and the gas through a heat exchange layer, such as layer 550 depicted in FIG. 9. In certain embodiments, the garment 920 includes a plurality of temperature regulators 924. The plurality of temperature regulators may be operationally coupled such that the target temperature of each regulator is substantially the same.

Figure 18A:
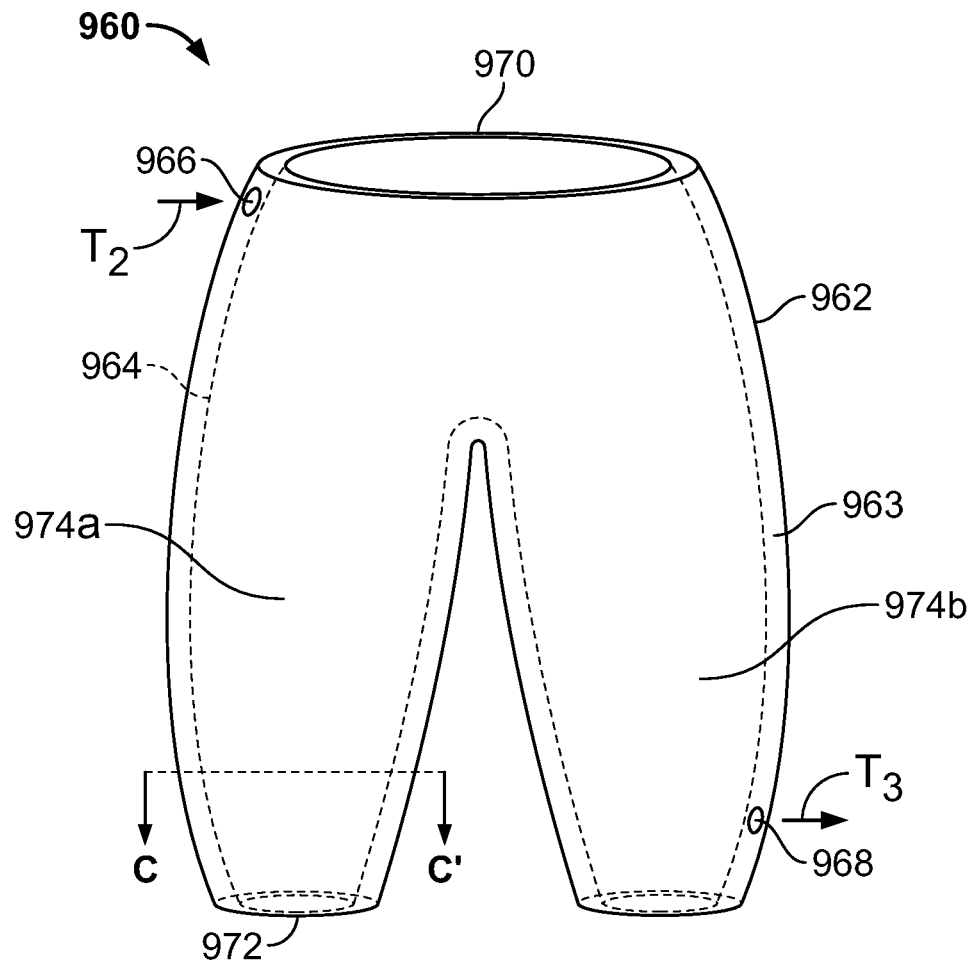
FIGS. 18A-18B depict a temperature regulation garment.
Figure 18B:
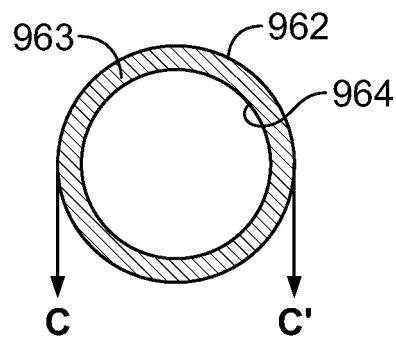

FIGS. 18A-18B depict an additional temperature regulating garment 960 shaped like a pair of pants, having at least one sleeve 974. The garment 960, as depicted, includes a plurality of sleeves 974a and 974b. The garment 960 includes an outer layer 962 and an inner layer 964. The space 963 between the outer layer 962 and inner layer 964 forms a gas chamber, as shown in the cross-sectional view of C-C' depicted in FIG. 18B. In certain embodiments, the garment 960 includes clasps or fasteners, such as waistband 970 and cuff 972, to hold the garment in place during therapy. In practice, the gas at temperature $T_2$ enters the gas chamber 963 of the garment 960 through an entry site 966. The garment 960 can be configured to deliver gas directly to the injury site, as previously described. For example, inner layer 962 may include a hole or aperture or a plurality of holes or apertures, as depicted in FIGS. 7A-7C, FIGS. 8A-8C, and FIGS. 12A-12C. In practice, the hole or aperture is located in the sleeve 974. In certain embodiments, the holes or apertures are placed near or directly over the injury site. In certain implementations, the placement of the holes or apertures is customized to the patient and determined by the location and size of the injury site.

In certain embodiments, the garment inner layer 964 is a heat exchange layer, similar to layer 550 depicted in FIG. 9, configured to transfer heat between the injury site and the gas. The inner layer 964 is constructed of a material that allows heat flow between the injury site and the gas. For example, inner layer 964 may be foil, Mylar, composite, or any other suitable material.

In certain embodiments, the inner layer 964 is constructed of a compressive fabric to provide compression to the injury site. The material also allows heat exchange between the injury site and the gas due to its material composition and structure. For example, the material may be porous, semi-porous, or woven.

In practice, the gas exits the garment 960 through release valve 968 at temperature $T_3$. Release valve 968 may include one or more valves, apertures, or perforations. For example, garment 960 may include a plurality of perforations distributed across outer layer 962. In alternative embodiments, the release valve 968 automatically opens when the gas in chamber 963 exceeds a predetermined pressure.

In FIGS. 15-18, the garments have been depicted for use on the legs and torso. However, the garments can be adapted for application to or exclusion of any part of the patient anatomy, including, but not limited to, the legs, arms, chest, back, shoulders, neck, buttocks, hands, and feet using the systems and methods described herein. The garments may also include electrical stimulation elements, such as electrodes and controllers as depicted in FIGS. 8A-8C, FIG. 10, and FIGS. 12A-C. In certain embodiments, one or more of the temperature regulator, blower, controller, battery, power source, electrical stimulation controller, electrode, or other system elements is integrated on or in the garments described above.

Fluids delivered to the therapy site through any of the systems or methods disclosed herein can be sterilized to prevent infections or the spread of disease. For example, a patient receiving cooling or heating therapy may have an open wound at the therapy site or elsewhere on the body that should be kept clean and free of infectious agents, such as bacteria, viruses, fungi, volatile organic compounds, chemicals, or other airborne pathogens. With water-based therapies, water may leak, spill, or condense at the therapy site and increase the likelihood of infection, cause discomfort, or dampen the dressing, which would need to be changed. Water can also damage furniture, cause electrical components to malfunction, or otherwise damage the system or surroundings.

Figure 19:
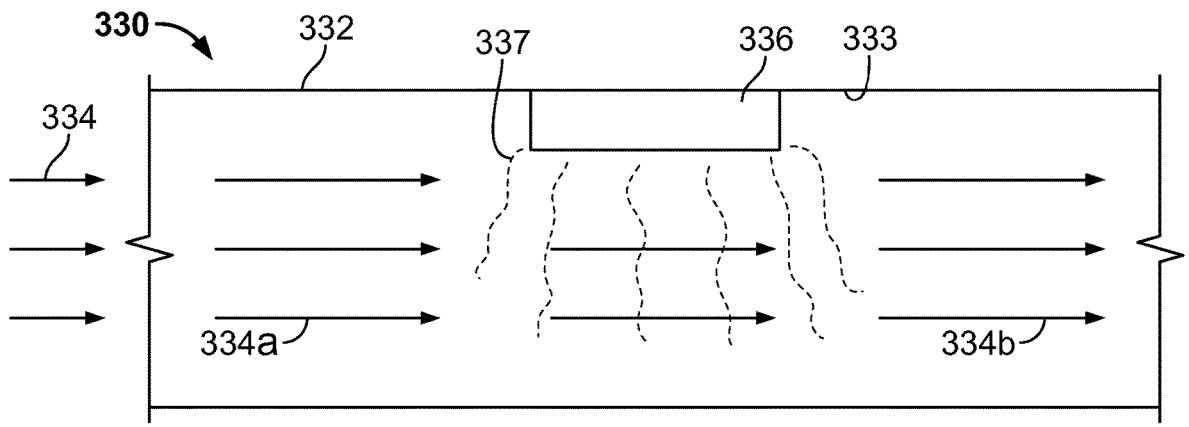
FIGS. 19-21 depict methods of sterilizing a gas or fluid.
Figure 20:
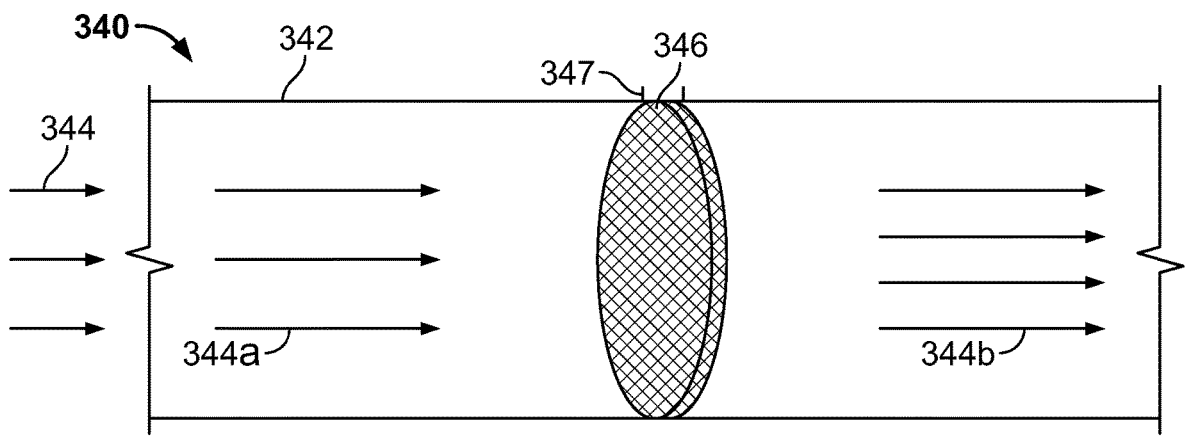
Figure 21:
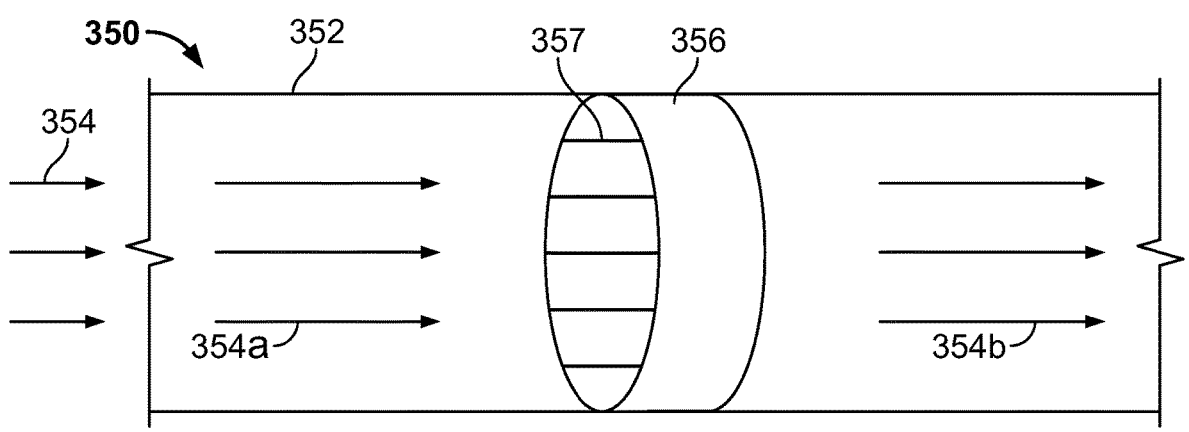

Sterilization systems may be used to address these issues. In general, the sterilization systems include one or more devices positioned with respect to the therapy systems and methods so as to reduce, deactivate, or eliminate infectious agents in the therapy fluid. In certain implementations, the sterilization devices are included within or near the fluid flow path and contact or apply to the fluid prior to the fluid entering the therapy pad (e.g., within the flow tube that enters the pad). In embodiments where the fluid is gas-based and contacts the patient directly (e.g., FIG. 7A-8C), sterilization of the gas prior to entering the pad may be particularly important. FIGS. 19-21 illustrate devices and methods for sterilizing a gas or other fluid used in the systems and methods. FIG. 19 shows a sterilization unit 330 comprising a flow channel 332 through which a gas 334 flows. The flow channel 332 includes an ultraviolet (UV) light source 336, such as a UV diode or germicidal bulb disposed on or about the channel 332 (in this case, disposed about the exterior of the channel wall 333). Preferably, the UV light source 336 emits light 337 at a wavelength between about 240 nanometers (nm) and 280 nm. In certain embodiments, the light source 336 emits light 337 at a wavelength between about 150 nm and 200 nm. The light source 336 may emit light 337 at a plurality of wavelengths, including, but not limited to approximately 185 nm and 254 nm.

In practice, the gas 334 enters the channel 332 as unsterilized gas 334a. The unsterilized gas 334a flows along the channel 332 and through the emitted light 337 from the light source 336, which kills or renders harmless microorganisms such as bacteria, viruses, and fungi present in the unsterilized gas 334a to provide sterilized gas 334b. The sterilized gas 334b is delivered to the therapy site, such as site 112, as described herein.

FIG. 20 depicts a sterilization unit 340 with a filter 346. The filter is disposed inside the fluid channel 342. The filter 346 traps particulate matter, microparticles (i.e., particles having a size less than 100 microns), and microorganisms including, but not limited to, bacteria, viruses, and fungi. In certain embodiments, the filter 346 includes fibers. For example, the filter 346 may be a high-efficiency particulate air (HEPA) filter, ultra low penetration air (ULPA) filter, activated carbon filter, or other filtration system. In certain embodiments, the filter 346 is removable from the system 340, and can be cleaned or replaced. For example, the flow channel 342 includes an upper slot 347 that receives a filter, such as the filter 346. The filter 346 con be removed and replaced when desired. Filter 346 (or any other sterilization device, for example those discussed or illustrated herein) may be installed within a disposable fluid flow module that can be removably connected within the tubing or other flow architecture of the therapy system and disposed after its useful life has expired.

In practice, the gas 344 enters the channel 342 as unsterilized gas 344a. The unsterilized gas 344a flows along the channel 342 and through the filter 346, which traps particulate matter, microparticles, and microorganisms such as bacteria, viruses, and fungi. The gas 344 emerges through the filter as sterilized gas 344b. The sterilized gas 344b is delivered to the therapy site, such as site 112, as described herein.

FIG. 21 depicts a sterilization unit 350 with an ionization purifier 356. The ionization purifier includes electrically charged surfaces 357. As the unsterilized air 354a flows through the channel 352, the airborne particles and microorganisms are removed from the air 354a by ionization or electrostatic attraction to the charged surfaced 357 to provide sterilized air 354b, which is delivered to the therapy site, such as site 112, as described herein. In certain embodiments, the ionization purifier 356 produces ozone to purify the gas 354.

The sterilization units may be used in any combination or subcombinations. For example, air can be purified by combining a UV sterilization unit, as depicted in FIG. 19, with a filtration unit, as depicted in FIG. 20. Other sterilization methods may also be used, including, but not limited to, photocatalytic oxidation, polarized-media electronic air cleaning, and liquid ionization purifiers.

Figure 22:
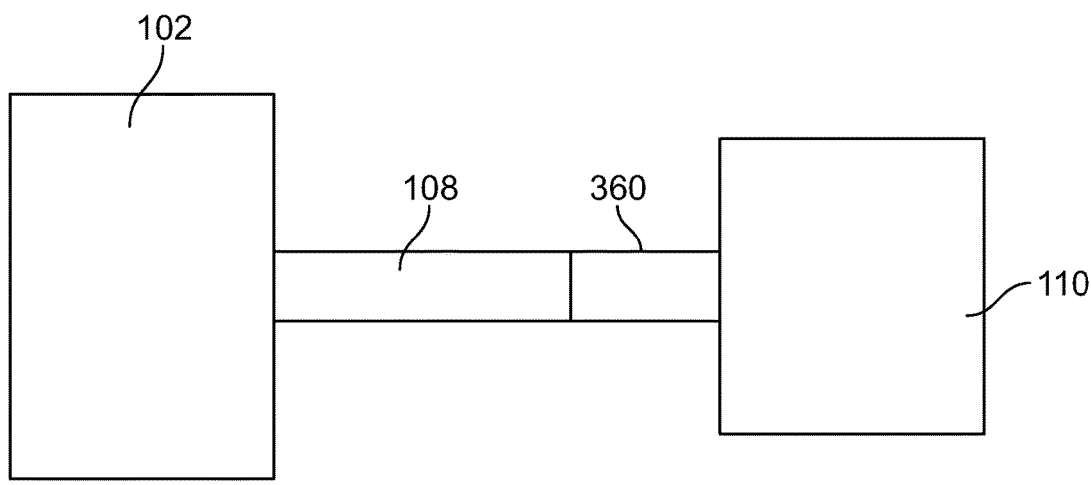
FIG. 22 depicts a temperature control system with an integrated sterilization unit.

FIG. 22 depicts a temperature control system with an integrated sterilization unit 360. The sterilization unit may contain one or more sterilization devices, such as the UV sterilization unit 330, filter sterilization unit 340, ionization purifier sterilization unit 3340, or other devices. The temperature regulator 102 is coupled to the flow tube 108. In preferred embodiments, the sterilization system 360 is disposed along the tube 108 near the pad 110 to sterilize the gas immediately before delivery to the pad 110 to ensure that the gas is clean and sterile as it is delivered to the therapy site. In certain embodiments, the sterilization system 360 is coupled to the temperature regulator 102. That coupling may be permanent, or modular and removable. For example, the sterilization unit 360 may be configured with a sterilization device in a disposable module that is installed for use within the flow architecture prior to the pad 110 and then is removed when the sterilization device has reached the end of its useful life, for example when the filter or purifier is full or a certain amount of energy has been emitted by a UV source.

Although primarily described in the context of temperature-controlled gas therapy, the systems and methods described herein may also provide temperature-controlled therapy using other fluids, including, but not limited to, liquids such as water. For example, the systems and methods described herein may provide closed-loop, temperature-controlled circulation systems for liquids.

Figure 23A:
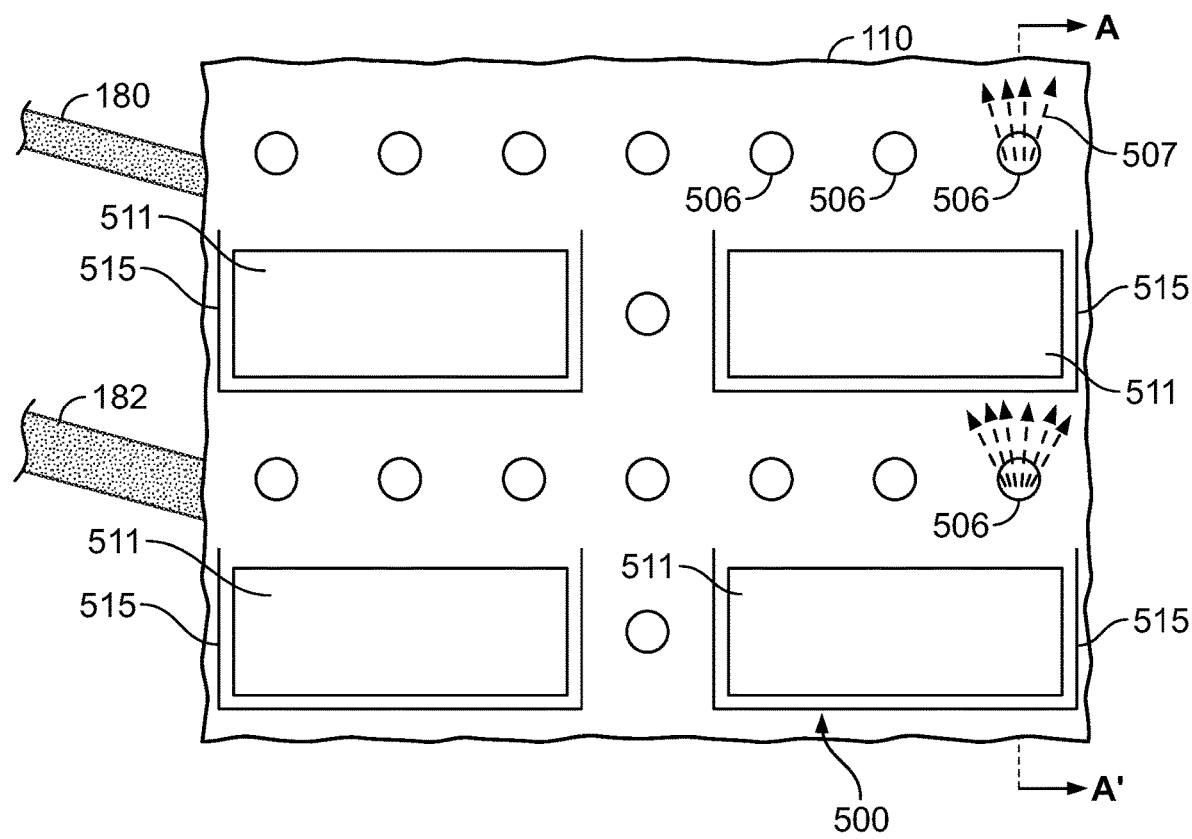
FIGS. 23A-25B depict temperature control systems with temperature maintenance packs.
Figure 23B:
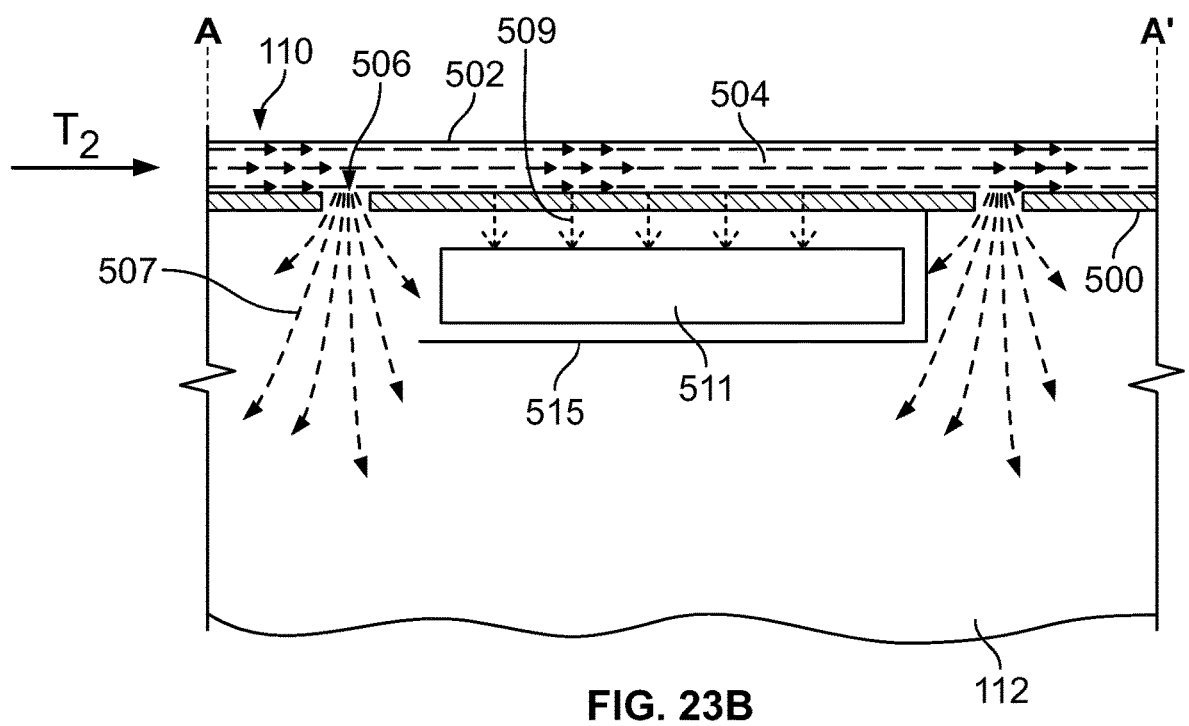
Figure 23C:
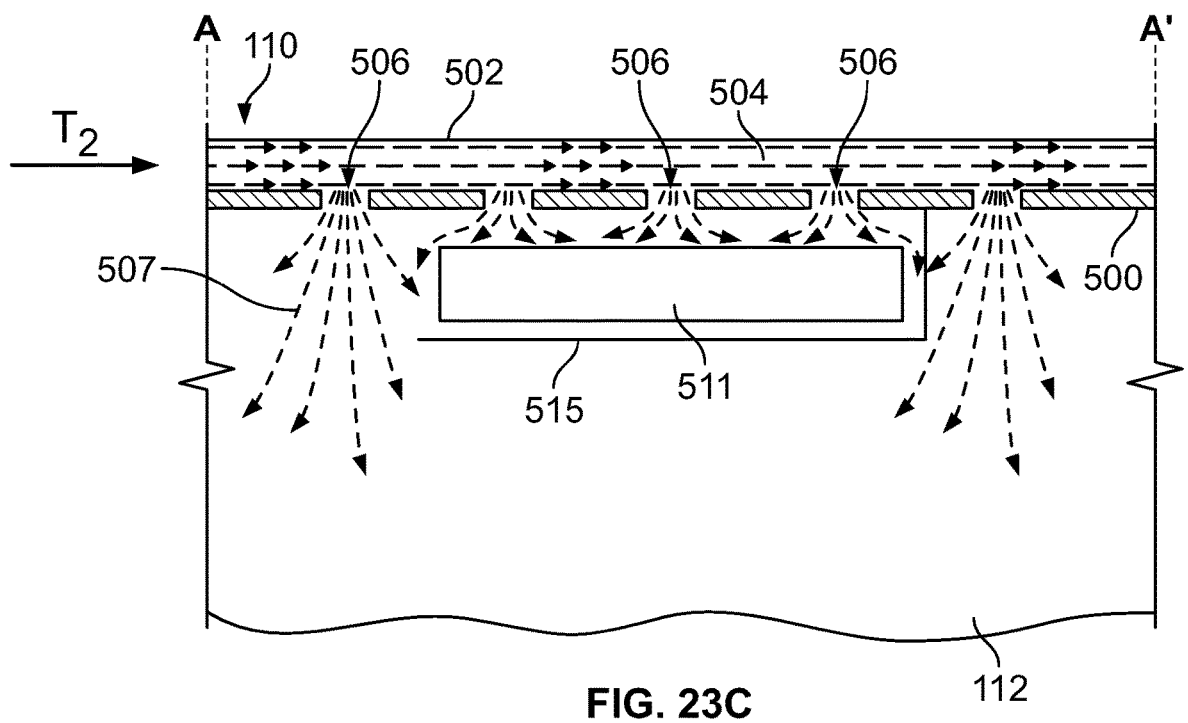

In certain embodiments, the temperature control system uses one or more temperature maintenance packs. In certain implementations one or more maintenance packs are integrated within a therapy pad, such as those disclosed herein. FIGS. 23A, 23B, and 23C depict front and cross sectional views (along line A-A') of an example therapy pad 110 configured with a plurality of temperature maintenance packs 511 to provide cold therapy (or heating therapy) to the patient. In alternative embodiments, a single maintenance pack 511 is used. As shown, the orthopedic wrap 110 has a flow channel 504 disposed between the inner layer 500 that forms a lower face of the flow channel 504, and upper layer 502 that forms an upper boundary or a backing of the flow channel 504. The packs 511 are disposed below or along the inner face 500 of the wrap 110 in pockets 515 of the pad 110. In certain embodiments, the pockets 515 partially or fully enclose the packs 511. The wrap 110 is held to the patient, for example, around the patient's knee, by a plurality of straps 180 and 182. In certain embodiments, the packs 511 are pliable and conform to the therapy site. For example, the packs 511 may contain a liquid or gel sealed in a flexible enclosure.

As shown in FIG. 23B, the gas 507 at a therapy temperature $T_2$ flows into the fluid channel 504 (for example, from the gas output line 108), travels through the channel 504, and contacts the packs 511. As indicated, a plurality of apertures or holes 506 are in fluid communication with the channel 504. The holes 506 are disposed along the inner face 500 of the wrap 110 between the packs 511 and the fluid channel 504, allowing fluid communication between the therapy gas and the patients injury site 112. The plurality of holes 506 are preferably disposed about at least two sides of the temperature maintenance pack. As fluid flows along the channel 504, convection heat exchange 509 occurs between the gas 504 and the packs 511, to help provide additional temperature control. The holes 506 allow gas 507 to flow along fluid channel 504 to regulate the temperature of the packs 511. In practice, the packs 511 are placed in pockets 515 near holes 506 so that gas 507 can have convective heat exchange 509 with the packs 511. The gas 507 flows through the holes 506 and disperse within the interior of the pad so the gas 507 contacts the patient's tissue at the therapy site 112 (for example as shown and discussed in relation to FIGS. 7A-8C). In certain embodiments, the gas 507 contacts the pack 511 after exiting the channel 504.

FIG. 23C depicts an alternative embodiment, in which a temperature maintenance pack 511 is disposed near or directly beneath the holes 506 such that gas 507 flows throw the holes 506, contacts the packs 511, exits pockets 515, disperses within the interior of the pad 110 to contact the patient's tissue at the therapy site 112. In practice, the pockets 515 are thermally conductive to allow heat transfer between the injury site 112 and the temperature maintenance packs 511 for effective temperature-controlled therapy of the injury site 112. In certain embodiments, the pockets 515 are permeable to the gas 507.

The temperature maintenance packs 511 preferably have a high specific heat capacity (e.g., greater than about 2000 J/Kg-K) to provide even heating or cooling to the patient. The packs 511 may include sealed liquids or gels, including, but not limited to water, glycols, hydroxyethyl cellulose, or silica in a sealed, flexible enclosure. The packs 511 may be cooled or heated before placement in the pad (for example, in a refrigerator, freezer, or microwave), and the gas 507 flowing around the packs 511 maintains the temperature of the packs 511 at the appropriate level. Conventional temperature maintenance packs must be removed from the therapy site to recharge them to the desired temperature. Additionally, conventional temperature packs change temperature during the therapy session and generally approach room temperature, which limits the effectiveness of the temperature regulation of the therapy site. In contrast, the temperature of the packs 511 is maintained by gas 507 so that the packs 511 can be used continuously at the desired temperature.

Figure 24:
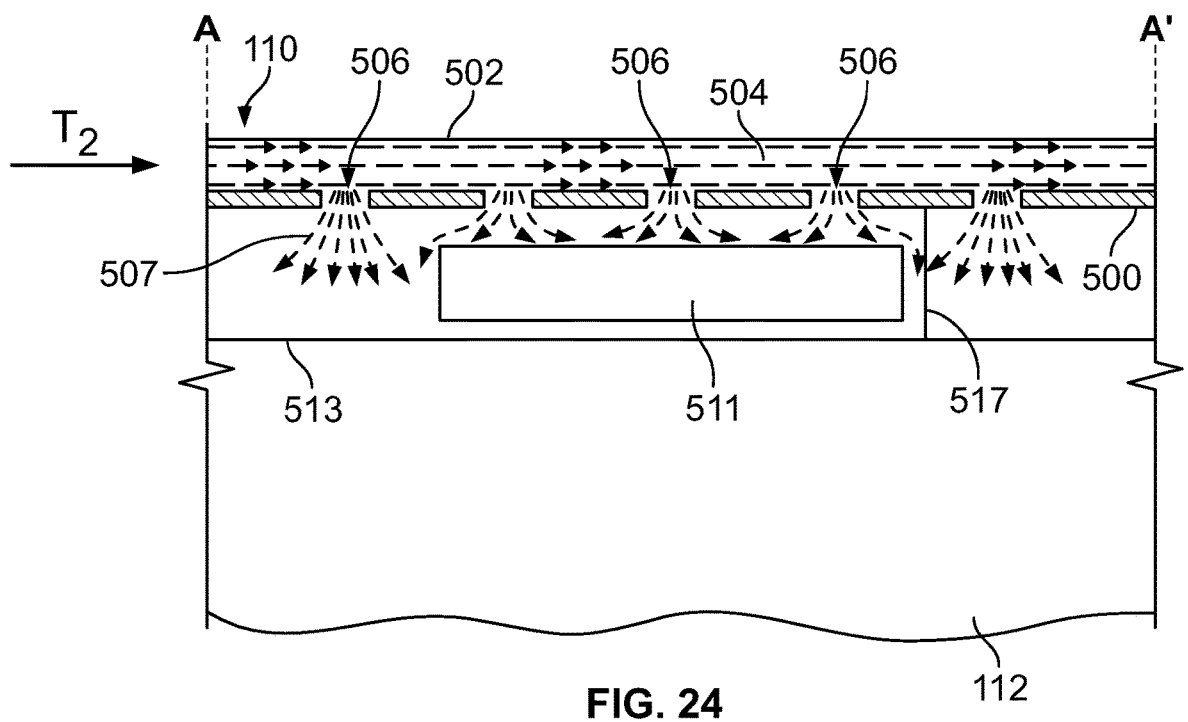

FIG. 24 depicts a cross-sectional view of an alternative embodiment of pad 110 with a temperature maintenance pack 511 and heat exchange layer 513. A plurality of temperature maintenance packs 511 may be used. The pack 511 is disposed between the inner face 500 and heat exchange layer 513 in pocket 517. The gas 507 flows throw the holes 506, contacts the pack 511, exits pocket 517, and disperses along the heat exchange layer 513. In certain embodiments, the pocket 517 fully encloses the pack 511. In certain embodiments, the pocket 517 is permeable to the gas 507. The pocket 517 may be formed as a seam through heat exchange layer 513 and inner face 500.

Heat exchange layer 513 covers the pack 511 and contacts the therapy site 112. Cooling or heating occurs at the patient site by conduction and convection across the heat exchange layer 513. The heat exchange layer 513 is constructed of a material with sufficiently high thermal conductivity (e.g., greater than about 0.1 W/m-K) to allow heat flow between the therapy site 112 and the packs 112. For example, the heat exchange layer 513 may be foil, Mylar, composite, mesh, or any other suitable material. In certain embodiments, the layer 513 is gas or fluid impermeable, such that the gas 507 does not directly contact the therapy site 112. The gas 507 is directed back to the temperature regulator (such as to regulator 102 through return line 212) a closed loop for recirculation. In alternative embodiments, the heat exchange layer 513 is at least semi-permeable to the gas 507, and the gas 507 flows through the layer 513 to the therapy site 112. For example, the heat exchange layer 513 may include pores or be constructed of a fibrous or mesh material.

Figure 25A:
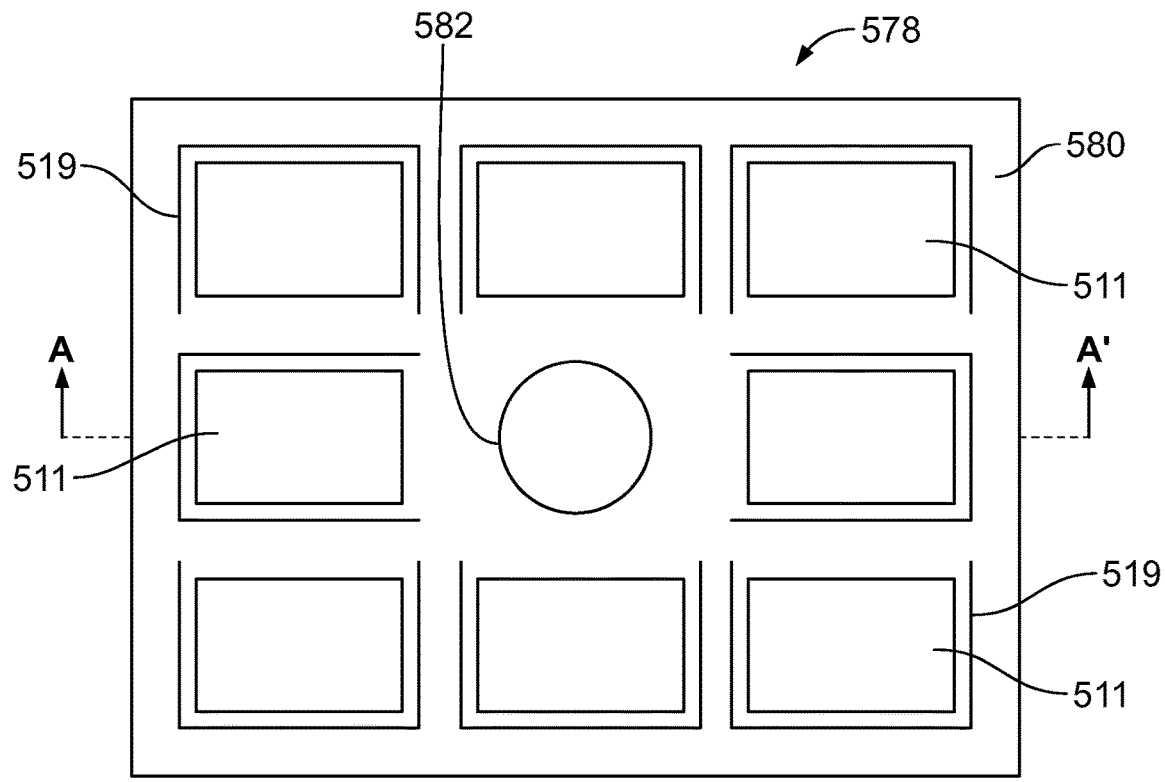
Figure 25B:
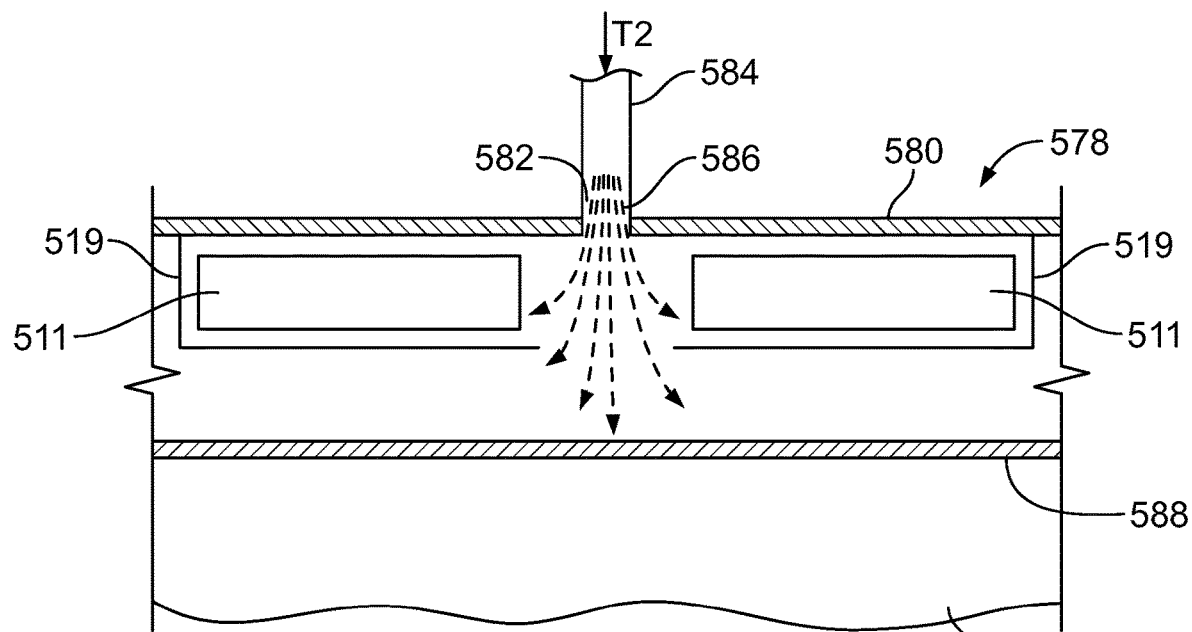

FIG. 25A depicts a pad 578 having an aperture 582 for delivering temperature controlled gas to the temperature maintenance packs 511. The packs 511 are disposed within pockets 519 along the inner face 580 of the wrap 578. FIG. 25B depicts a cross-sectional view of the pad 578 shown along the line A-A' of FIG. 25A. The gas 586 at a therapy temperature $T_2$ flows along tube 584 from the temperature regulator (such as regulator 102 through gas line 108) and through the aperture 582 to provide temperature-controlled gas 586 to the packs 511 and maintain the temperature of the packs 511 at the target temperature $T_2$. In certain embodiments, the pad 578 includes a heat exchange layer 588, which interfaces with the therapy site 112. The heat exchange layer 588 is similar to previously discussed heat exchange layers 513 and 550, in that it allows heat to flow by convection and by conduction between the therapy site 112 and the packs 112. In certain embodiments, the layer 588 is gas or fluid impermeable, such that the gas 586 does not directly contact the therapy site 112. The gas 586 may be directed back to the temperature regulator (such as to regulator 102 through return line 212) for recirculation. Preferably, the heat exchange layer 588 is at least semi-permeable to the gas 586, and the gas 586 flows through the layer 588 to the therapy site 112. For example, the heat exchange layer 588 may include pores or be constructed of a fibrous or mesh material.

It is to be understood that the foregoing description is merely illustrative, and is not to be limited to the details given herein. While several embodiments have been provided in the present disclosure, it should be understood that the disclosed systems, devices and methods and their components may be embodied in many other specific forms without departing from the scope of the disclosure.

Variations and modifications will occur to those of skill in the art after reviewing this disclosure, where disclosed features may be implemented in any combination and subcombinations (including multiple dependent combinations and subcombinations), with one or more other features described herein. The various features described or illustrated above, including any components thereof, may be combined or integrated in other systems, moreover, certain features may be omitted or not implemented.

Examples of changes, substitutions and alterations are ascertainable by one skilled in the art and to be made without departing from the scope of the information disclosed herein. All references cited herein are incorporated by reference in their entirety and made part of this application.

The invention claimed is:

1. A system for delivering a temperature-controlled gas to a therapy site comprising:
   a gas temperature regulator;
   a gas intake port;
   a first line configured to supply heated gas from the temperature regulator;
   a second line configured to supply cooled gas from the temperature regulator;
   a first valve configured to receive the heated gas from the first line, receive the cooled gas from the second line, and output a mixture of the heated gas and the cooled gas to a therapy pad at a controlled temperature; and
   the therapy pad, comprising:
      an insulating layer,
      a flow channel disposed behind and configured to distribute the mixture of the heated gas and the cooled gas to an inner face of the therapy pad,
      a lower frame configured to mate with the therapy site,
      a mesh layer disposed between the insulating layer and the lower frame and comprising a plurality of undulations configured to deliver the mixture of the heated gas and the cooled gas to the therapy site within the lower frame, and
      at least one electrostimulation electrode embedded within the inner face of the therapy pad, the at least one electrostimulation electrode having a first surface configured to make direct electrical contact with the therapy site and a second surface opposite the first surface configured to make direct physical contact with the mixture of the heated gas and the cooled gas within the flow channel.

2. The system of claim 1, wherein the gas intake port is a manifold in communication with ambient air.

3. The system of claim 1, wherein the gas intake port is in communication with stored or compressed gas.

4. The system of claim 1, wherein the gas temperature regulator comprises a cooling component and a heating component.

5. The system of claim 4, wherein the heating component and cooling component are disposed within a single housing.

6. The system of claim 1, wherein the gas temperature regulator is a Peltier device.

7. The system of claim 1, further comprising a temperature sensor configured to sense a temperature of one or both of:
   the mixture of the heated gas and the cooled gas; or
   the therapy site.

8. The system of claim 7, wherein the gas temperature regulator further comprises a controller configured to receive a signal from the temperature sensor and trigger an alarm when the signal indicates a temperature satisfying a predetermined temperature threshold.

9. The system of claim 1, comprising a temperature maintenance pack.

* * * * *